United States Patent
Zagury et al.

(10) Patent No.: US 11,198,851 B2
(45) Date of Patent: Dec. 14, 2021

(54) EX VIVO GENERATION OF γδ FOXP3⁺ REGULATORY T CELLS AND THERAPEUTIC USES THEREOF

(71) Applicants: INSERM (Institut National de la Sante et de la Recherche Medicale), Paris (FR); Medecine et Innovation, Paris (FR); Universite Paris Diderot—Paris 7, Paris (FR); Centre National de la Recherche Scientifique (CNRS), Paris (FR)

(72) Inventors: Daniel Zagury, Paris (FR); Helene Le Buanec, Paris (FR); Sophie Duchez, Paris (FR); Valerie Schiavon, Paris (FR); Armand Bensussan, Paris (FR)

(73) Assignees: INSERM (INSTITUT NATIONAL DE LA SANTE ET DE LA RECHERE MEDICALE), Paris (FR); MEDECINE ET INNOVATION, Paris (FR); UNIVERSITE DE PARIS, Paris (FR); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 135 days.

(21) Appl. No.: 16/320,764

(22) PCT Filed: Aug. 4, 2017

(86) PCT No.: PCT/EP2017/069826
§ 371 (c)(1),
(2) Date: Jan. 25, 2019

(87) PCT Pub. No.: WO2018/024896
PCT Pub. Date: Feb. 8, 2018

(65) Prior Publication Data
US 2019/0161729 A1    May 30, 2019

(30) Foreign Application Priority Data
Oct. 28, 2016  (EP) .................................. 16196428

(51) Int. Cl.
*C12N 5/0783* (2010.01)
*A61K 35/17* (2015.01)

(52) U.S. Cl.
CPC ............ *C12N 5/0637* (2013.01); *A61K 35/17* (2013.01); *C12N 2501/01* (2013.01); *C12N 2501/065* (2013.01); *C12N 2501/15* (2013.01); *C12N 2501/22* (2013.01); *C12N 2501/2302* (2013.01); *C12N 2501/2304* (2013.01); *C12N 2501/2307* (2013.01); *C12N 2501/2315* (2013.01); *C12N 2501/515* (2013.01); *C12N 2501/599* (2013.01); *C12N 2501/72* (2013.01); *C12N 2501/727* (2013.01); *C12N 2501/999* (2013.01); *C12N 2502/1121* (2013.01)

(58) Field of Classification Search
None
See application file for complete search history.

(56) References Cited

U.S. PATENT DOCUMENTS

2013/0195919 A1    8/2013   Von Andrian

FOREIGN PATENT DOCUMENTS

| EP | 2 408 934 B1 | 11/2014 |
|---|---|---|
| WO | 2009/037723 A1 | 3/2009 |
| WO | 2010/022341 A1 | 2/2010 |
| WO | 2013/050596 A1 | 4/2013 |

OTHER PUBLICATIONS

Gu et al., 2014, J. Immunol. Methods. vol. 402: 82-87.*
Pastor et al., 2013, Nat Rev Mol Cell Biol. vol. 14: 341-356.*
Gergori et al., 2010, Blood, vol. 116: 935-944.*
Singal et al., 1999. Blood. vol. 93: 4059-4070.*
Mahic et al.,2006, J. Immunol. vol. 177: 246-254.*
Sassone-Corsi, 2012, Cold Spring Herb Perspect Biol, pp. 1-3.*
Martinet et al., 2010, Biochem. Pharm. vol. 80: 838-845.*
Chaudhury et al., 2009, IUBMB Life vol. 61: 929-939.*
Delgoffe et al., 2009, Immunology, vol. 127: 459-465.*
Tran et al.; "Selective expression of latency-associated peptide (LAP) and IL-1 receptor type I/II (CD121a/CE121b) on activated human FOXP3+ regulatory T cells allows for their purification from expansion cultures"; Blood, vol. 113, No. 2, May 21, 2009, pp. 5125-5133.
Ohkura et al.; "FOXP3+ regulatory T cells: control of FOXP3 expression by pharmacological agents"; Trends in Pharmacological Sciences, vol. 32, No. 3, Mar. 1, 2011, pp. 158-166.
Baratelli et al.; "Prostaglandin E2 Induces FOXP3 Gene Expression and T Regulatory Cell Function in Human CD4+ T Cells"; The Journal of Immunology, vol. 175, No. 3, Jul. 20, 2005, pp. 1483-1490.

(Continued)

Primary Examiner — Amy E Juedes
(74) Attorney, Agent, or Firm — W&C IP

(57) ABSTRACT

The present invention relates to a method for ex vivo generating and expanding γδ Foxp3⁺ regulatory T cells, and therapeutic uses thereof. The inventors performed the induction of Foxp3+ expression in ex vivo human induced tumor-antigen specific CD4+ TCRγδ unrestricted T cells and the induction of autologous CD8-mediated T-cell responses against tumor-antigen specific FOXP3 expressing CD4+ TCRγδ unrestricted T cells. The inventors developed a method to ex vivo generated and expanded antigen specific Foxp3 expressing CD3+ TCRγδ+ unrestricted T cells, committed to exclusively exert regulatory activity, whichever culture condition of stimulation is. In particular, the present invention relates to a method for generating ex vivo γδ Foxp3+ regulatory T cells having the following phenotype: CD3+ TCRγδ+ Foxp3+.

4 Claims, 9 Drawing Sheets
Specification includes a Sequence Listing.

(56) References Cited

OTHER PUBLICATIONS

Scott et al.; "Patterns of membrane TcRαβ and TcRd chain expression by normal blood CD4+CD8−, CD4−CD8dim+ and CD4−CD8− lymphocytes"; Immunology, vol. 70, Jan. 1, 1990, pp. 351-356.

Castella et al.; "Immune Modulation by Zoledronic Acid in Human Myeloma: An Advantageous Cross-Talk between Vγ9Vø2 T Cells, αβ CD8+ T Cells, Regulatory T Cells, and Dendritic Cells"; The Journal of Immunology, vol. 187, No. 4, Jul. 13, 2011, pp. 1578-1590.

Orsini et al.; "Zoledronic acid modulates maturation of human monocyte-derived dendritic cells"; Experimental Biology and Medicine, vol. 236, No. 12, Dec. 1, 2011, pp. 1420-1426.

Peng et al.; "Tumor-Infiltrating γø T Cells Suppress T and Dendritic Cell function via Mechanisms Controlled by a Unique Toll-like Receptor Signaling Pathway"; Immunity, vol. 27, No. 2, Aug. 1, 2007, pp. 334-348.

Chen et al.; "Conversion of Peripheral CD4+CD25—Naive T Cells to CD4+CD25+ Regulatory T Cells by TGF-β Induction of Transcription Factor Foxp3"; The Journal of Experimental Medicine, vol. 198, No. 12, Dec. 15, 2003, pp. 1875-1886.

* cited by examiner

| | CD3+ T Cells isolated from PBMCs | | | | | | TIL isolated from breast tumor | |
|---|---|---|---|---|---|---|---|---|
| | CD3+ TCR αβ MHCII restricted T cells | | CD3+ invTCR Vα24+ CD1-restricted T cells | | CD3 TCR γδ MHCI unrestricted T cells | | CD3 TCR γδ MHCI unrestricted T cells | |
| | FOXP3- | FOXP3+ | FOXP3- | FOXP3+ | FOXP3- | FOXP3+ | FOXP3- | FOXP3+ |
| | 91.85/1970 | 8.15/18923 | 90.5/1734 | 9.5/75477 | 99/1872 | 1/6712 | 77.3/94 | 22.7/1968 |
| | (%/MFI) | (%/MFI) | (%/MFI) | (%/MFI) | (%/MFI) | (%/MFI) | (%/MFI) | (%/MFI) |
| CD4+ | 67.9/16683 | 96.8/14792 | 17.7/14324 | 92.3/16528 | 1.86/9676 | 44.9/10640 | 37.5/10508 | 98.8/11126 |
| CD127+ (Treg) | 60.6/1800 | 10.1/2141 | 91.5/2883 | 8.28/1945 | 54.2/1790 | 69.7/2196 | ND | ND |
| CD25+ (Treg) | 6.44/1041 | 77.8/3109 | 3.91/1045 | 80.5/10388 | 3.14/990 | 19.1/1786 | 4.87/2131 | 67.5/4317 |
| CTLA4+ | 3.34/627 | 45.2/830 | 0/- | 71.6/1918 | 0.228/671 | 18.1/736 | 11.3/1043 | 93.4/3016 |
| CD56+ (Vα24+ NKT) | 1.48/814 | 0.263/911 | 30.7/830 | 2.37/990 | 11.1/774 | 8.04/733 | 4.29/582 | 7.67/463 |
| CD161+ (Vα24+ NKT) | 11.7/1568 | 5.39/1133 | 92.5/4435 | 15.4/2101 | 71.1/1706 | 49.6/1251 | ND | ND |
| demethylated FOXP3 promoter | <10% | >50% | <10% | >50% | ND | ND | ND | ND |
| Enrichment of H3AcK9 in FOXP3 promoter region | <5% | >=20% | <5% | >=20% | ND | ND | ND | ND |

FIG. 1

|  |  | Foxp3- |  |  |  | Foxp3+ (%) | Foxp3+ |  |  |  |
|---|---|---|---|---|---|---|---|---|---|---|
|  |  | Foxp3- (%) | CD4+ (%) | CD8+ (%) | CD4+CD8+ (%) | CD4-CD8- (%) |  | CD4+ (%) | CD8+ (%) | CD4+CD8+ (%) | CD4-CD8- (%) |
| PBMCs | Subject 1 | >99 | 4.02 | 29.5 | 0.255 | 66.2 | bg | NA | NA | NA | NA |
|  | Subject 2 | >98.7 | 9.08 | 23.6 | 2.05 | 65.3 | bg | NA | NA | NA | NA |
|  | Subject 3 | >98.3 | 3.64 | 21.2 | 0.364 | 74.8 | bg | NA | NA | NA | NA |
| BC biopsies TIL | Patient 1 | 86.9 | 12.8 | 27.8 | 1.65 | 57.8 | 13.1 | 87.3 | 3.03 | 9.7 | 0 |
|  | Patient 2 | 79.8 | 13.4 | 46 | 3.08 | 37.4 | 19.7 | 76.8 | 17 | 3.57 | 2.68 |

FIG. 3

LUMINAL A Tumor (good prognostic)
CD3+ CD4+ TCR αβ MHCII restricted
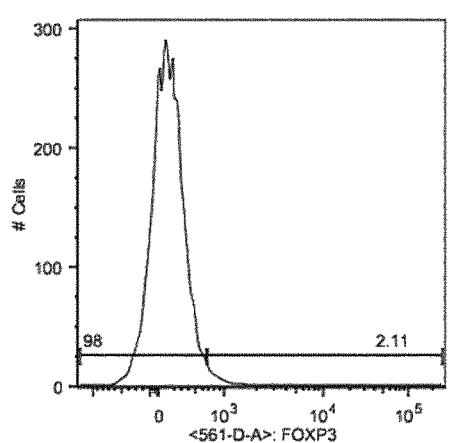
CD3+ CD4+ TCR γδ MHC unrestricted
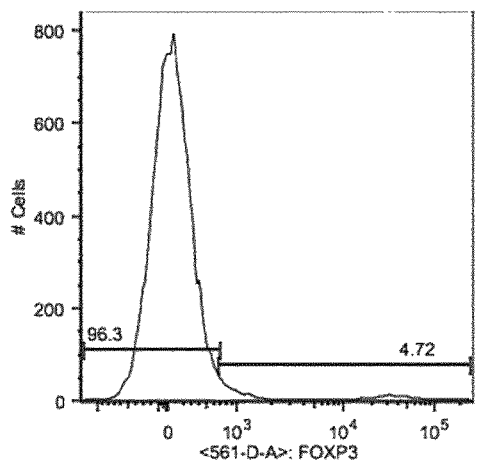
LUMINAL B Tumor (poor clinical outcome)
CD3+ CD4+ TCR αβ MHCII restricted
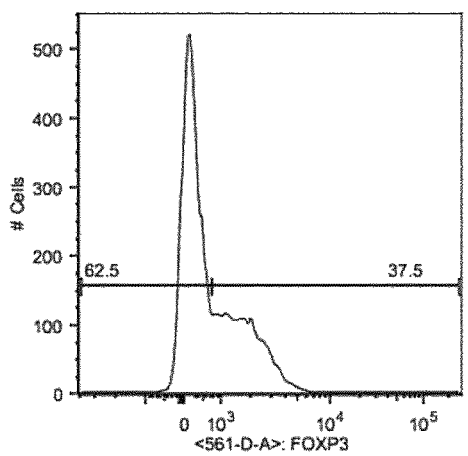
CD3+ CD4+ TCR γδ MHC unrestricted
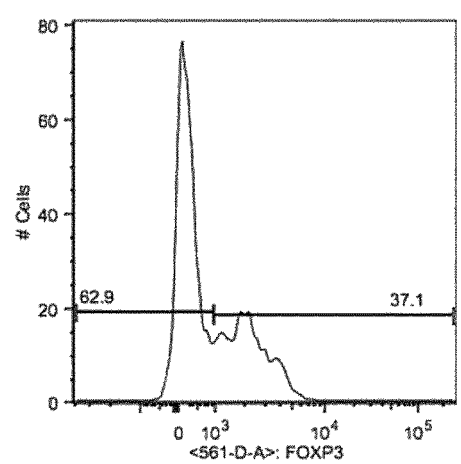
FIG. 7

EX VIVO GENERATION OF γδ FOXP3+ REGULATORY T CELLS AND THERAPEUTIC USES THEREOF

FIELD OF INVENTION

The present invention relates to an ex vivo method for generating and expanding γδ Foxp3+ regulatory T cells and therapeutic uses thereof.

BACKGROUND OF INVENTION

γδ T cells account for about 1-5% of circulating T cells and operate at the interface between innate and adaptive immunity. These cells possess a combination of innate and adaptive immune cell qualities rendering them attractive for exploitation in therapies, in particular cancer immunotherapy. Indeed, γδ T cells can produce inflammatory cytokines, directly lyse infected or malignant cells and establish a memory response to attack pathogen upon re-exposure. Unlike classical αβ T cells, Vγ9Vδ2 T cells, the major subset of the circulating γδ T cells pool, recognize nonprocessed antigens such as phosphomonoesters. This recognition is mediated by the TCR and is not restricted by MHC molecules.

It has been shown in the art the regulatory γδ T cells expressing Foxp3 can be induced under opportune antigen stimulation and cytokines (Casetti et al. JI 2009, 183:3574-3577). These Foxp3+ regulatory γδ T cells are capable of suppressive activity.

As of today, no method has been suggested in the art to ex vivo expand these Foxp3+ regulatory γδ T cells for their therapeutic exploitation.

The present invention thus provides a method for ex vivo generating and expanding Foxp3+ γδ regulatory T cells and therapeutic uses of said Foxp3+ γδ regulatory T cells.

SUMMARY

The present invention relates to a method for generating ex vivo γδ Foxp3+ regulatory T cells having the following phenotype: CD3+ TCR γδ+ Foxp3+, comprising
  culturing CD3+ TCR γδ+ T cells in the presence of a γδ T cell activator and the following agents: i) an cAMP (Cyclic adenosine monophosphate) activator, ii) a TGFβ (Transforming growth factor beta) pathway activator, iii) a mTOR inhibitor, optionally iv) at least one cytokine selected in the group of IL-2, IL-7, IL-15 and TSLP, and optionally v) at least one TET enzymes activator (preferably selected from vitamin C and a NaHS hydrogen sulfide releasing agent) and/or at least one DNMT inhibitor (such as, for example, RG108, DAC or 5AC), for at least 5 days.

In one embodiment, the γδ T cell activator is a polyclonal γδ T cell activator, preferably an anti-TCR γδ antibody or a non-peptide phosphoantigen.

In another embodiment, the γδ T cell activator is an antigen-specific γδ T cell activator, preferably tolerogenic dendritic cells (DCs) and pulsed with at least one bisphosphonate, preferably at least one aminobiphosphonate.

In one embodiment of the present invention, the cAMP activator is selected from the group comprising prostaglandin E2 (PGE2), an EP2 or EP4 agonist, a membrane adenine cyclase activator or a metabotropic glutamate receptors agonist.

In one embodiment, the TGFβ pathway activator is selected from the group comprising TGFβ, bone morphogenetic proteins (BMPs), growth and differentiation factors (GDFs), anti-müllerian hormone (AMH), activin and nodal.

In one embodiment, the mTOR inhibitor is selected from the group comprising rapamycin, rapamycin analogs, wortmannin; theophylline; caffeine; epigallocatechin gallate (EGCG), curcumin, resveratrol; genistein, 3,3-diindolylmethane (DIM), LY294002 (2-(4-morpholinyl)-8-phenyl-4H-1-benzopyran-4-one), PP242, PP30, Torin1, Ku-0063794, WAY-600, WYE-687, WYE-354, GNE477, NVP-BEZ235, PI-103, XL765 and WJD008.

In one embodiment, the method of the present invention further comprises an expansion step, wherein the γδ Foxp3+ regulatory T cells obtained by the generation method as described above are cultured in the presence of a γδ T cell activator and the following agents: i) an cAMP (Cyclic adenosine monophosphate) activator, ii) a TGFβ (Transforming growth factor beta) pathway activator, iii) a mTOR inhibitor, optionally iv) at least one cytokine selected in the group of IL-2, IL-7, IL-15 and TSLP, and optionally v) at least one TET enzymes activator (preferably selected from vitamin C and a NaHS hydrogen sulfide releasing agent) and/or at least one DNMT inhibitor (such as, for example, RG108, DAC or 5AC), for at least 5 days.

Another object of the present invention is an ex vivo generated γδ Foxp3+ regulatory T cell population obtainable by the method as described hereinabove.

A further object of the present invention relates to an ex vivo generated and expanded γδ Foxp3+ regulatory T cell population obtainable by the method according to the invention.

The present invention also relates to an ex vivo generated γδ Foxp3+ regulatory T cell population that remains functionally stable in inflammatory condition.

The present invention further relates to an immunogenic product comprising inactivated γδ Foxp3+ regulatory T cells. or blebs of γδ Foxp3+ regulatory T cells or immunogenic dendritic cells loaded with blebs of γδ Foxp3+ regulatory T cells.

The present invention also provides a pharmaceutical composition comprising inactivated γδ Foxp3+ regulatory T cells and at least pharmaceutically acceptable excipient or blebs of γδ Foxp3+ regulatory T cells or immunogenic dendritic cells loaded with blebs of γδ Foxp3+ regulatory T cells.

Another object of the present invention is a vaccine composition comprising inactivated γδ Foxp3+ regulatory T cells and at least one adjuvant or blebs of γδ Foxp3+ regulatory T cells or immunogenic dendritic cells loaded with blebs of γδ Foxp3+ regulatory T cells.

A further object of the present invention relates to the immunogenic product, pharmaceutical composition or vaccine composition according to the invention for use in treating cancer.

The present invention also relates to a pharmaceutical composition comprising γδ Foxp3+ regulatory T cells and at least one pharmaceutically acceptable excipient.

The present invention further relates to a pharmaceutical composition as described hereinabove for use in cell therapy.

A further object of the present invention is a pharmaceutical composition as described hereinabove for use in treating inflammatory or autoimmune diseases or for preventing transplant rejection or graft versus host disease (GVHD).

Definitions

As used herein, "regulatory T cells" or "Treg" refers to cells capable of suppressive activity (i.e. inhibiting proliferation of conventional T cells), either by cell-cell contact or by MLR suppression (Mixed Lymphocytes Reaction). These cells include different subpopulations including but not limited to, MHCII restricted CD4$^+$ Foxp3$^+$ regulatory T cells, γδ Foxp3$^+$ regulatory T cells and invariant Foxp3$^+$ regulatory T cells.

As used herein, "invariant Foxp3$^+$ regulatory T cells" refers to cells having the following phenotype: CD3$^+$Vα24$^+$ Foxp3$^+$. These cells recognize non peptide lipid antigens under CD1 restriction.

As used herein, γδ Foxp3$^+$ regulatory T cells" refers to cells having the following phenotype: γδTCR$^+$ Foxp3$^+$. These cells recognize non peptide phospho antigens with no MHC (major histocompatibility complex) restriction.

As used herein, "MHCII restricted CD4$^+$ Foxp3$^+$ regulatory T cells" refers to cells having the following phenotype: CD4$^+$CD25$^+$Foxp3$^+$. These cells can be identified by their αβ TCR (T cell receptor) and recognize peptides (including foreign or self peptides) presented by restricted MHC class II (major histocompatibility complex class II) molecules.

As used herein, the term "treatment" refers to therapeutic treatment and prophylactic and preventive measures, wherein the object is to prevent or slow down (lessen, diminish) the targeted pathological disorder or condition. Those in need of treatment include those already with the disorder as well as those prone to have the disorder or those in whom the disorder is to be prevented. A subject or mammal is successfully "treated" for a disease if, after receiving a therapeutic amount of γδ Foxp3$^+$ regulatory T cells or a therapeutically amount of inactivated γδ Foxp3$^+$ regulatory T cells according to the present invention, the patient shows observable and/or measurable reduction in or absence of one or more of the following: reduction in the number of pathogenic cells; reduction in the percent of total cells that are pathogenic; and/or relief to some extent, of one or more of the symptoms associated with the specific disease or condition; reduced morbidity and mortality, and improvement in quality of life issues. The above parameters for assessing successful treatment and improvement in the disease are readily measurable by routine procedures familiar to a physician.

As used herein, "therapeutically effective amount" refers to the number of γδ Foxp3$^+$ regulatory T cells or of inactivated γδ Foxp3$^+$ regulatory T cells that is aimed at inducing a therapeutic response, without causing significant negative or adverse side effects to the target. A therapeutically effective amount may be administered prior to the onset of the disease to be treated, for a prophylactic or preventive action. Alternatively or additionally, the therapeutically effective amount may be administered after initiation of the disease to be treated, for a therapeutic action.

As used herein, "therapeutic response" refers to a therapeutic benefit induced by the γδ Foxp3$^+$ regulatory T cell therapy or the γδ Foxp3$^+$ regulatory T cell vaccination in a subject. A therapeutic response may include the fact of (1) delaying or preventing the onset of the disease to be treated; (2) slowing down or stopping the progression, aggravation, or deterioration of one or more symptoms of the disease to be treated; (3) bringing about ameliorations of the symptoms of the disease to be treated; (4) reducing the severity or incidence of the disease to be treated; or (5) curing the disease to be treated.

As used herein, "about" preceding a figure means more or less 10% of the value of said figure.

As used herein, "subject or patient" refers to a mammal, preferably a human. In the present invention, the terms subject and patient may be used with the same meaning. Examples of non-human mammal include a pet such as a dog, a cat, a domesticated pig, a rabbit, a ferret, a hamster, a mouse, a rat and the like; a primate such as a chimp, a monkey, and the like; an economically important animal such as cattle, a pig, a rabbit, a horse, a sheep, a goat. In one embodiment, the subject is awaiting the receipt of, or is receiving medical care or was/is/will be the object of a medical procedure, or is monitored for the development of a disease. In one embodiment, the subject is an adult (for example a subject above the age of 18). In another embodiment, the subject is a child (for example a subject below the age of 18). In one embodiment, the subject is a male. In another embodiment, the subject is a female.

As used herein, "allogeneic cells" refers to cells isolated from one subject (the donor) and infused in another (the recipient or host).

As used herein, "autologous cells" refers to cells that are isolated and infused back into the same subject (recipient or host).

DETAILED DESCRIPTION

The present invention relates to a method for generating ex vivo γδ Foxp3$^+$ regulatory T cells.

In one embodiment, the method for generating ex vivo γδ Foxp3$^+$ regulatory T cells, comprises:
culturing CD3$^+$ TCR γδ$^+$ T cells, preferably CD3$^+$ TCR γδ$^+$ CD45RA$^+$ T cells, in the presence of a γδ T cell activator and the following agents: i) an cAMP (Cyclic adenosine monophosphate) activator, ii) a TGFβ (Transforming growth factor beta) pathway activator, iii) a mTOR inhibitor, optionally iv) at least one cytokine selected in the group of IL-2, IL-7, IL-15 and TSLP (Thymic stromal lymphopoietin), and optionally v) at least one TET enzymes activator and/or at least one DNMT inhibitor, for at least 5 days,
thereby obtaining a population of γδ Foxp3$^+$ regulatory T cells ex vivo generated, preferably from γδ naïve (CD45RA$^+$) T cells.

In one embodiment, the CD3$^+$ TCR γδ$^+$ T cells, preferably CD3$^+$ TCR γδ$^+$ CD45RA$^+$ T cells, are obtained by any technic well known in the art from a blood sample. In one embodiment, the CD3$^+$ TCR γδ$^+$ T cells, preferably CD3$^+$ TCR γδ$^+$ CD45RA$^+$ T cells, are isolated from PBMCs (peripheral blood mononuclear cells) by flow cytometry. In one embodiment, the CD3$^+$ TCR γδ$^+$ T cells, preferably CD3$^+$ TCR γδ$^+$ CD45RA$^+$ T cells, may be isolated from frozen PBMCs.

In one embodiment, the obtainment of isolated CD3$^+$ TCRγδ$^+$ T cells, preferably CD3$^+$ TCRγδ$^+$ CD45RA$^+$ T cells, may be improved by an optional first to a purification step. The CD3$^+$ TCRγδ$^+$ T cells, preferably CD3$^+$ TCRγδ$^+$ CD45RA$^+$ T cells, are stimulated with antigen pulsed tolerogenic DCs (for example ovalbumin pulsed tolerogenic DCs) in the presence of soluble anti-CD28 and anti-CD40 antibodies. In one embodiment, the time of stimulation ranges between 1 hour and 24 hours, preferably between 10 hours and 20 hours, more preferably during about 16 hours. After stimulation, cells are washed, for example with PBS, and stained with anti-CD154 and anti-CD4 antibodies for sorting. The purified CD3$^+$ TCRγδ$^+$ CD154$^+$ T cells are enriched and may be used for the following activation step.

In one embodiment, the CD3$^+$ TCR γδ$^+$ T cells are activated in the presence of an γδ T cell activator. Said γδ T cell activator can be a polyclonal γδ T cell activator or an antigen-specific γδ T cell activator.

In the present invention, the polyclonal γδ T cell activator is a TCR γδ activator. Examples of TCR γδ activator include, but are not limited to, anti-TCR γδ antibody such as purified mouse anti-human TCR γδ Clone B1 (ref 555715, BD Biosciences), anti-human TCR γδ antibody (ref 331209, Biolegend), monoclonal TCR γδ antibody (ref NBP2-22489 or NBP2-22510, Novus Biologicals), anti-mouse γδ CR antibody (ref 12-5711-81, eBioscience), TCR γδ antibody (ref MAB7297, R&D Systems), anti-T-Cell receptor γδ antibody (ref ABIN2372990, antibodies-online), anti-TCR gamma+TCR delta antibody (ref ab25663, Abcam), anti-γδ CR antibody clone IMMU510 (Beckman Coulter); non peptide phosphoantigens (also called phosphorylated non peptide antigens) including but not limited to isoprenyl pyrophosphate (IPP), (E)-4-hydroxy-3-methyl-but-2-enyl diphosphate (HMB-PP) and analogs thereof (such as bromohydrin diphosphate (BrHPP) and 2-methyl-3-butenyl-1-pyrophosphate (2M3B1PP)); $F_1$-ATPase; apolipoprotein A-I; *Mycobacterium tuberculosis*; UL16-binding protein 4 (ULBP4); CD1c; CD1d tetramers loaded with sulphatide; Endothelial protein C receptor (EPCR), Lipoexapeptides; Phycoerythrin, Histidyl-tRNA synthase and butyrophilin 3A1.

In another embodiment, the polyclonal γδ T cell activator is MHC Class-I related A (MICA).

In another embodiment, the polyclonal γδ T cell activator is immunogenic apoptotic bodies from cancer cells or blebs from cancer cells or derived from tissue lysate.

Cancer cells may derive from tumor biopsy or from expansion of circulatory cancer cells.

Immunogenic apoptotic bodies from cancer cells may be obtained for example with anthracyclines including doxorubicin, daunorubicin, idarubicin and mitoxanthrone; oxaliplatin, UVC or γ-radiation treated cancer cells releasing apoptotic bodies or can be directly isolated from anthracyclines including doxorubicin, daunorubicin, idarubicin and mitoxanthrone; oxaliplatin; UVC or γ-radiation treated cancer.

Blebs constitute an important immunogenic particle. They are heterogenous vesicle formed at the surface of apoptotic cells. In one embodiment, the size of blebs ranges from 0.05-5 μm, preferably from 0.1 to 1 μm. Various Immunogenic cell death (ICD) inducers can induce the release of blebs from apoptotic or autophagic cells, such as, for example, irradiation at 5000 rad, and several antineoplastic agents, including doxorubicin, oxaliplatin and cisplatin. Immunogenic cancer cell blebs may, in particular, be obtained from apoptotic cancer cells or from cancer cell autophagy following treatment by chemical or physical inducers.

In one embodiment, the polyclonal γδ T cell activator is an anti-TCRγδ antibody or a non peptide phosphoantigen such as isoprenyl pyrophosphate (IPP).

In one embodiment, the polyclonal γδ T cell activator, preferably the anti-TCR γδ antibody, is soluble in the culture medium. In another embodiment, the polyclonal γδ T cell activator is coated to the culture plate.

In one embodiment, the polyclonal γδ T cell activator, preferably the anti-TCR γδ antibody, is used in the presence of feeder cells, preferably autologous feeder cells.

Feeder cells include, but are not limited to, ΔCD3 cells (T cell-depleted accessory cells), irradiated PBMCs, irradiated DCs, artificial APCs (antigen presenting cells), Sf9 cells, insect cells, a pool of PBMCs or a pool of B cells from different subjects, KCD40L cells EBV-transformed B cell lines and EBV-transformed lymphoblastoid cells (LCL).

Preferably, the feeder cells used in the invention are ΔCD3 cells that are isolated by negative selection from PBMCs by incubation with anti-CD3-coated beads and then irradiated at 3000 rad.

In one embodiment, the ratio T cells/feeder cells ranges from about 1:100 to about 1:10 000, preferably from 1:1 000 to 1:5 000. Within the scope of the invention, the expression "from 1:100 to 1:10 000" includes, without limitation, 1:100, 1:200, 1:300, 1:400, 1:500, 1:600, 1:700, 1:800, 1:900, 1:1 000, 1:1 250, 1:1 500, 1:1 750, 1:2 000, 1:2 250, 1:2 500, 1:2 750, 1:3 000, 1:3 250, 1:3 500, 1:3 750, 1:4 000, 1:4 250, 1:4 500, 1:4 750, 1:5 000, 1:5 250, 1:5 500, 1:5 750, 1:6 000, 1:6 250, 1:6 500, 1:6 750, 1:7 000, 1:7 250, 1:7 500, 1:7 750, 1:8 000, 1:8 250, 1:8 500, 1:8 750, 1:9 000, 1:9 250, 1:9 500, 1:9 750 and 1:10 000.

In the present invention, the antigen-specific γδ T cell activator is tolerogenic dendritic cells (DCs).

As used herein, "tolerogenic DCs" refers to DCs capable to induce tolerance. In one embodiment, tolerogenic DCs are capable of secreting more suppressive cytokines such as IL-10 and TGFβ than proinflammatory cytokines such as IL-12, IL-23 or TNFα. In one embodiment, DCs are defined as tolerogenic when they secrete IL-10 and IL-12 in a ratio IL-10:IL-12>1.

In one embodiment, tolerogenic DCs express on their surface the major histocompatibility (MHC) class Ia and/or MHC class Ib. The MHC class Ia presentation refers to the "classical" presentation through HLA-A, HLA-B and/or HLA-C molecules whereas the MHC class Ib presentation refers to the "non-classical" antigen presentation through HLA-E, HLA-F, HLA-G and/or HLA-H molecules.

In one embodiment, tolerogenic DCs express 50% of MHC class Ia molecules and 50% of MHC class Ib molecules on their surface. In one embodiment, tolerogenic DCs express 45% of MHC class Ia molecules and 55% of MHC class Ib molecules on their surface. In one embodiment, tolerogenic DCs express 40% of MHC class Ia molecules and 60% of MHC class Ib molecules on their surface. In one embodiment, tolerogenic DCs express 35% of MHC class Ia molecules and 65% of MHC class Ib molecules on their surface. In one embodiment, tolerogenic DCs express 30% of MHC class Ia molecules and 70% of MHC class Ib molecules on their surface. In one embodiment, tolerogenic DCs express 25% of MHC class Ia molecules and 75% of MHC class Ib molecules on their surface. In one embodiment, tolerogenic DCs express 20% of MHC class Ia molecules and 80% of MHC class Ib molecules on their surface. In one embodiment, tolerogenic DCs express 15% of MHC class Ia molecules and 85% of MHC class Ib molecules on their surface. In one embodiment, tolerogenic DCs express 10% of MHC class Ia molecules and 90% of MHC class Ib molecules on their surface. In one embodiment, tolerogenic DCs express 5% of MHC class Ia molecules and 95% of MHC class Ib molecules on their surface. In one embodiment, tolerogenic DCs express only MHC class Ib molecules on their surface.

In one embodiment, tolerogenic DCs express 50% of HLA-A, HLA-B and/or HLA-C molecules and 50% of HLA-E molecules on their surface. In one embodiment, tolerogenic DCs express 45% of HLA-A, HLA-B and/or HLA-C molecules and 55% of HLA-E molecules on their surface. In one embodiment, tolerogenic DCs express 40% of HLA-A, HLA-B and/or HLA-C molecules and 60% of HLA-E molecules on their surface. In one embodiment, tolerogenic DCs express 35% of HLA-A, HLA-B and/or HLA-C molecules and 65% of HLA-E molecules on their surface. In one embodiment, tolerogenic DCs express 30% of HLA-A, HLA-B and/or HLA-C molecules and 70% of HLA-E molecules on their surface. In one embodiment, tolerogenic DCs express 25% of HLA-A, HLA-B and/or HLA-C molecules and 75% of HLA-E molecules on their surface. In one embodiment, tolerogenic DCs express 20% of HLA-A, HLA-B and/or HLA-C molecules and 80% of HLA-E molecules on their surface. In one embodiment, tolerogenic DCs express 15% of HLA-A, HLA-B and/or HLA-C molecules and 85% of HLA-E molecules on their surface. In one embodiment, tolerogenic DCs express 10% of HLA-A, HLA-B and/or HLA-C molecules and 90% of HLA-E molecules on their surface. In one embodiment, tolerogenic DCs express 5% of HLA-A, HLA-B and/or HLA-C molecules and 95% of HLA-E molecules on their surface. In one embodiment, tolerogenic DCs express only HLA-E molecules on their surface.

Methods for obtaining tolerogenic DCs are well-known in the art. An exemplary method is the generation of tolerogenic DCs from CD14$^+$ monocytes. For example, CD14$^+$ monocytes are cultured in the presence of GM-CSF and IL-4, or in the presence of GM-CSF and IFNα, for the generation of immature DCs.

Methods for inhibiting MHC class Ia molecules expression or inducing the expression of HLA-E molecules on the surface of tolerogenic DCs are well-known.

The inhibition of the TAP transporter (transporter associated with antigen processing) leads to a decreased expression of MHC class Ia molecules thereby promoting HLA-E molecules expression on the surface of tolerogenic DCs.

Exemplary methods to inhibit the TAP transporter in the endoplasmic reticulum include, but are not limited to, CRISPR-CAS-9 technology, silencing RNA, transfected DCs with the UL-10 viral protein from the CMV (cytomegalovirus) or the use of viral proteins.

Examples of viral proteins able to inhibit the TAP transporter include, but are not limited to, HSV-1 ICP47 protein, varicella-virus UL49.5 protein, cytomegalovirus US6 protein or gammaherpesvirus EBV BNLF2a protein.

Another method is the use of a chemical product to inhibit the expression of MHC class Ia molecules without changing HLA-E expression on the surface of tolerogenic DCs. Examples of chemical products include, but are not limited to, 5'-methyl-5'-thioadenosine or leptomycin B.

The tolerogenic DCs are pulsed in the presence of at least one bisphosphonate, preferably aminobiphosphonate, during about 24 h. Examples of biphosphonate include, but are not limited to, zoledronic acid (or zoledronate), pamidronic acid, alendronic acid, risedronic acid, ibandronic acid, incadronic acid, etidronic acid, tiludronic acid, a combination thereof, a salt thereof and a hydrate thereof. Preferably, the biphosphanate is zoledronic acid or zoledronate.

In one embodiment, biphosphonate, in particular zoledronic acid, is used at a concentration from 10 nM to 50 µM. Within the scope of the invention, the expression "from 10 nM to 50 µM" includes, without limitation, 50 nM, 100 nM, 250 nM, 500 nM, 750 nM, 1 µM, 10 µM, 20 µM, 30 µM, 40 µM, 50 µM.

In one embodiment, the cAMP activator added in the culture allows the activation of the cAMP pathway. Examples of cAMP activator include, but are not limited to PGE2 (prostaglandin E2), an EP2 or EP4 agonist, a membrane adenine cyclase activator such as forskolin, or metabotropic glutamate receptors agonists. Examples of PGE2 include, but are not limited to, PGE2 of ref P5640 or P0409 (Sigma-Aldrich), PGE2 of ref 2296 (R&D Systems), PGE2 of ref 2268 (BioVision), PGE2 of ref 72192 (Stemcell), PGE2 of ref ab144539 (Abcam), and PGE2 of ref 14010 (Cayman Chemical).

In one embodiment, the cAMP activator, preferably PGE2, is used at a concentration ranging from 0.01 µM to 10 µM. Within the scope of the invention, the expression "from 0.01 µM to 10 µM" includes, without limitation, 0.02 µM, 0.03 µM, 0.04 µM, 0.05 µM, 0.06 µM, 0.07 µM, 0.08 µM, 0.09 µM, 0.1 µM, 0.2 µM, 0.3 µM, 0.4 µM, 0.5 µM, 0.6 µM, 0.7 µM, 0.8 µM, 0.9 µM, 1 µM, 1.5 µM, 2 µM, 2.5 µM, 3 µM, 3.5 µM, 4 µM, 4.5 µM, 5 µM, 6 µM, 7 µM, 8 µM, 9 µM. In certain embodiments, PGE2 is at a concentration ranging from 0.03 µM to 1.5 µM.

In one embodiment, the TGFβ pathway activator added in the culture allows the activation of the TGFβ β pathway. Examples of TGF TGFβ pathway activators include, but are not limited to, TGFβ β family (TGFβ1, TGFβ2, TGFβ3), bone morphogenetic proteins (BMPs), growth and differentiation factors (GDFs), anti-müllerian hormone (AMH), activin, and nodal. Examples of TGFβ include, but are not limited to, TGFβ1 of ref T7039 (Sigma-Aldrich), TGFβ2 of ref T2815 (Sigma-Aldrich), TGFβ3 of ref T5425 (Sigma-Aldrich), human TGFβ1 of ref P01137 (R&D system), human TGFβ1 of ref 580702 (Biolegend), TGFβ1 of ref HZ-1011 (HumanZyme), human TGFβ1 of ref 14-8348-62 (Affymetrix eBioscience).

In one embodiment, the pathway activator is used at a concentration ranging from 1 ng/ml to 20 ng/ml. Within the scope of the invention, the expression "from 1 ng/ml to 20 ng/ml" includes, without limitation, 2 ng/ml, 2.5 ng/ml, 3 ng/ml, 3.5 ng/ml, 4 ng/ml, 4.5 ng/ml, 5 ng/ml, 5.5 ng/ml, 6 ng/ml, 6.5 ng/ml, 7 ng/ml, 7.5 ng/ml, 8 ng/ml, 8.5 ng/ml, 9 ng/ml, 9.5 ng/ml, 10 ng/ml, 11 ng/ml, 12 ng/ml, 13 ng/ml, 14 ng/ml, 15 ng/ml, 16 ng/ml, 17 ng/ml, 18 ng/ml, 19 ng/ml. In certain embodiments, TGFβ is at a concentration ranging from 2.5 ng/ml to 7.5 ng/ml.

In one embodiment, the mTOR inhibitor added in the culture allows the inhibition of the mTOR pathway. Examples of mTOR inhibitor include, but are not limited to, rapamycin (also named sirolimus) and its analogs (termed rapalogs); wortmannin; theophylline; caffeine; epigallocatechin gallate (EGCG); curcumin; resveratrol; genistein; 3,3-diindolylmethane (DIM); LY294002 (2-(4-morpholinyl)-8-phenyl-4H-1-benzopyran-4-one); PP242; PP30; Torin1; Ku-0063794; WAY-600; WYE-687; WYE-354; and mTOR and PI3K dual-specificity inhibitors such as GNE477, NVP-BEZ235, PI-103, XL765 and WJD008. Examples of rapamycin include, but are not limited to, rapamycin of ref R0395 (Sigma-Aldrich), rapamycin of ref S1039 (Selleckchem), rapamycin of ref 1292 (Tocris), rapamycin of ref R-5000 (LC Laboratories), rapamycin of ref tlrl-rap (InvivoGen), rapamycin of ref ab120224 (Abcam), rapamycin of ref R0395 (Sigma-Aldrich).

Examples of compounds of the same chemical class than rapamycin used clinically include, but are not limited to, Everolimus (code name RAD001), Temsirolimus (code name CCI-779, NSC 683864), Zotarolimus (code name ABT-578).

In one embodiment, the mTOR inhibitor, preferably rapamycin, is used at a concentration ranging from 0.1 nM to 50 nM. Within the scope of the invention, the expression "from 0.1 nM to 50 nM" includes, without limitation, 0.2 nM, 0.3 nM, 0.4 nM, 0.5 nM, 0.6 nM, 0.7 nM, 0.8 nM, 0.9 nM, 1 nM, 2 nM, 3 nM, 4 nM, 5 nM, 6 nM, 7 nM, 8 nM, 9 nM, 10 nM, 11 nM, 12 nM, 13 nM, 14 nM, 15 nM, 16 nM, 17 nM, 18 nM, 19 nM, 20 nM, 21 nM, 22 nM, 23 nM, 24 nM, 25 nM, 26 nM, 27 nM, 28 nM, 29 nM, 30 nM, 31 nM, 32 nM, 33 nM, 34 nM, 35 nM, 36 nM, 37 nM, 38 nM, 39 nM, 40 nM, 41 nM, 42 nM, 43 nM, 44 nM, 45 nM, 46 nM, 47 nM, 48 nM, 49 nM.

In one embodiment, at least one cytokine selected from IL-2, IL-7, IL-15 and TSLP can be added in the culture.

In one embodiment, IL-2 is used at a concentration ranging from 10 IU/ml to 1000 IU/ml. Within the scope of the invention, the expression "from 10 IU/ml to 1000 IU/ml" includes, without limitation, 15 IU/ml, 20 IU/ml, 25 IU/ml, 30 IU/ml, 35 IU/ml, 40 IU/ml, 45 IU/ml, 50 IU/ml, 55 IU/ml, 60 IU/ml, 65 IU/ml, 70 IU/ml, 75 IU/ml, 80 IU/ml, 85 IU/ml, 90 IU/ml, 95 IU/ml, 100 IU/ml, 150 IU/ml, 200 IU/ml, 250 IU/ml, 300 IU/ml, 350 IU/ml, 400 IU/ml, 450 IU/ml, 500 IU/ml, 550 IU/ml, 600 IU/ml, 650 IU/ml, 700 IU/ml, 750 IU/ml, 800 IU/ml, 850 IU/ml, 900 IU/ml, 950 IU/ml. In certain embodiments, IL-2 is used at a concentration ranging from 50 IU/ml to 250 IU/ml.

In one embodiment, IL-7 is used at a concentration ranging from 1 ng/ml to 100 ng/ml. Within the scope of the invention, the expression "from 1 ng/ml to 100 ng/ml" includes, without limitation, 1 ng/ml, 5 ng/ml, 10 ng/ml, 15 ng/ml, 20 ng/ml, 25 ng/ml, 30 ng/ml, 35 ng/ml, 40 ng/ml, 45 ng/ml, 50 ng/ml, 55 ng/ml, 60 ng/ml, 65 ng/ml, 70 ng/ml, 75 ng/ml, 80 ng/ml, 85 ng/ml, 90 ng/ml, 95 ng/ml, 100 ng/ml.

In one embodiment, IL-15 is used at a concentration ranging from 1 ng/ml to 50 ng/ml. Within the scope of the invention, the expression "from 1 ng/ml to 50 ng/ml" includes, without limitation, 2 ng/ml, 3 ng/ml, 4 ng/ml, 5 ng/ml, 6 ng/ml, 7 ng/ml, 8 ng/ml, 9 ng/ml, 10 ng/ml, 15 ng/ml, 20 ng/ml, 25 ng/ml, 30 ng/ml, 35 ng/ml, 40 ng/ml, 45 ng/ml. In certain embodiments, IL-15 is used at a concentration ranging from 10 ng/ml to 30 ng/ml. In one embodiment, TSLP is used at a concentration ranging from 1 ng/ml to 100 ng/ml. Within the scope of the invention, the expression "from 1 ng/ml to 100 ng/ml" includes, without limitation, 1 ng/ml, 5 ng/ml, 10 ng/ml, 15 ng/ml, 20 ng/ml, 25 ng/ml, 30 ng/ml, 35 ng/ml, 40 ng/ml, 45 ng/ml, 50 ng/ml, 55 ng/ml, 60 ng/ml, 65 ng/ml, 70 ng/ml, 75 ng/ml, 80 ng/ml, 85 ng/ml, 90 ng/ml, 95 ng/ml, 100 ng/ml.

Examples of TET activators include but are not limited to vitamin C and NaHS hydrogen sulfide releasing agents (also known as H2S donors).

In one embodiment, vitamin C is used at a concentration ranging from 1 to 100 µg/ml.

In one embodiment, NaHS hydrogen sulfide releasing agent is used at a concentration ranging from 0.25 to 8 mM.

Examples of DNMT inhibitors include but are not limited to 2-(1,3-dioxo-1,2-dihydro-2H-isoindol-2-yl)-3-(1H-indol-3-yl) propanoic acid (RG108), 5-aza-2'-deoxycytidine (decitabine or DAC) and 5-azacytidine (5AC).

In one embodiment, RG108 is used at a concentration ranging from 20 to 500 µM.

In one embodiment, DAC is used at a concentration ranging from 0.1 to 2 µM.

In one embodiment, 5AC is used at a concentration ranging from 0.1 to 10 µM.

In one embodiment neutralizing antibodies can be added to the culture to prevent the generation of other populations of regulatory T cells.

Examples of neutralizing antibodies include, but are not limited to, anti-IFNγ, anti-IL-4, and/or anti-IL12 antibodies.

Examples of anti-IFNγ antibodies include, but are not limited to, Affymetrix eBioscience (Ref 14-7318), R&D systems (Ref MAB285), Novus Biologicals (Ref AF-485-NA).

Examples of anti-IL-4 antibodies include, but are not limited to, R&D Systems (Ref MAB304, MAB204, or MAB204), Affymetrix eBioscience (Ref 14-7048), GeneTex (Ref GTX10755).

Examples of anti-IL-12 antibodies include, but are not limited to, Affymetrix eBioscience (Ref 16-7129 or 16-8126), Biolegend (Ref 508803), R&D systems (Ref MAB219, AF-219, or AB-219).

In one embodiment, the culture medium used in the culture of the invention comprises (i) one or more pH buffering system(s); (ii) inorganic salt(s); (iii) trace element(s); (iv) free amino acid(s); (v) vitamin(s); (vi) hormone(s); (vii) carbon/energy source(s).

Examples of inorganic salts include, but are not limited to, calcium bromide, calcium chloride, calcium phosphate, calcium nitrate, calcium nitrite, calcium sulphate, magnesium bromide, magnesium chloride, magnesium sulphate, potassium bicarbonate, potassium bromide, potassium chloride, potassium dihydrogen phosphate, potassium disulphate, di-potassium hydrogen phosphate, potassium nitrate, potassium nitrite, potassium sulphite, potassium sulphate, sodium bicarbonate, sodium bromide, sodium chloride, sodium disulphate, sodium hydrogen carbonate, sodium dihydrogen phosphate, di-sodium hydrogen phosphate, sodium sulphate and a mix thereof.

Examples of trace elements include, but are not limited to, cobalt (Co), copper (Cu), iron (Fe), magnesium (Mg), manganese (Mn), molybdenum (Mo), nickel (Ni), selenium (Se), zinc (Zn) and the salts thereof.

Examples of free amino acids include, but are not limited to, L-alanine, L-arginine, L-asparagine, L-aspartic acid, L-cysteine, L-cystine, L-glutamine, L-glutamic acid, glycine, L-histidine, L-isoleucine, L-leucine, L-lysine, L-methionine, L-phenylalanine, L-proline, L-serine, taurine, L-threonine, L-tryptophan, L-tyrosine, L-valine and a mix thereof.

Examples of vitamins include, but are not limited to, biotin (vitamin H); D-calcium-pantothenate; choline chloride; folic acid (vitamin B9); myo-inositol; nicotinamide; pyridoxal (vitamin B6); riboflavin (vitamin B2); thiamine (vitamin B1); cobalamin (vitamin B12); acid ascorbic; α-tocopherol (vitamin E) and a mix thereof.

Examples of carbon/energy sources include, but are not limited to, D-glucose; pyruvate; lactate; ATP; creatine; creatine phosphate; and a mix thereof.

In one embodiment, the culture medium is a commercially available cell culture medium, in particular selected in a group comprising the IMDM (Iscove's Modified Dulbecco's Medium) from GIBCO® or the RPMI 1640 medium from GIBCO®.

In another embodiment, the culture medium is a serum-free culture medium such as the AIM-V medium from GIBCO®, the X-VIVO 10, 15 and 20 media from LONZA.

In another embodiment, the culture medium can be further supplemented with additional compound(s), in particular selected in a group comprising foetal bovine serum, pooled human AB serum, cytokines and growth factors; antibiotic(s), in particular selected in a group comprising penicillin, streptomycin and a mix thereof.

In one embodiment, the culture medium is IMDM.

In some particular embodiments, the culture medium comprises IMDM cell culture medium; from 1% (w/w) to 5% (w/w) of foetal bovine serum; from 10 IU/ml to 200 IU/ml of penicillin; from 10 IU/ml to 200 IU/ml of streptomycin; from 0.1 mM to 10 mM of a mixture of non-essential amino acids, in particular amino acids selected in a group comprising alanine, asparagine, aspartic acid, cysteine, glutamic acid, glutamine, glycine, proline, serine, and tyrosine; from 0.5 mM to 10 mM of glutamine from 10 mM to 25 mM of HEPES pH 7.6-7.8.

In one embodiment, the medium is a nTreg polarizing medium. The inventors define a "nTreg polarizing medium" as a medium such as RPMI medium comprising at least one cAMP activator as described hereabove, at least one TGFβ pathway activator as described here above and at least one mTor inhibitor as described hereabove. In a preferred embodiment, the "nTreg polarizing medium" refers to a RPMI medium comprising TGFβ, rapamycin and PGE2.

In another embodiment, the medium is an inflammatory medium. The inventors define an "inflammatory medium" as a medium such as IMDM comprising inflammatory cytokines such as for example IL-1β (10 ng/ml), IL-6 (30 ng/ml), IL-21 (50 ng/ml), IL-23 (30 ng/ml), IL-2 (100 UI/ml).

In one embodiment, the culture for generating the γδ Foxp3$^+$ regulatory T cells of the invention is performed during at least 5 days, at least 6 days, at least 7 days, at least 8 days. Within the scope of the invention, the expression "at least 5 days" includes, without limitation, 5 days, 6 days, 7 days, 8 days, 9 days, 10 days, 11 days, 12 days, 13 days, 14 days, 15 days.

In one embodiment, a portion of the culture medium is discarded once, twice, three times, four times or five times during the time course of the generation culture and replaced with the same volume of fresh culture medium. Within the scope of the invention the term "portion" is intended to mean at least 20% (v/v), at least 25% (v/v), at least 30% (v/v), at least 35% (v/v), at least 40% (v/v), at least 45% (v/v), at least 50% (v/v), at least 55% (v/v), at least 60% (v/v), at least 65% (v/v), at least 70% (v/v), at least 75% (v/v) of the volume of the culture medium. In certain embodiments, 40% (v/v) to 60% (v/v) of the volume of the culture medium of step a) is discarded. In certain embodiments, the volume that is discarded is replaced with an identical volume of fresh culture medium. Within the scope of the invention, the expression "fresh culture medium" refers to a culture medium that has not been in contact with any CD3+ T cells.

In one embodiment, the method for generating ex vivo γδ Foxp3$^+$ regulatory T cells, comprises:
  culturing CD3$^+$ TCR γδ$^+$ T cells, preferably CD3$^+$ TCR γδ$^+$ CD45RA$^+$ T cells, in the presence of autologous ΔCD3 feeder cells and coated anti-TCR γδ antibody and in the presence of the following agents: i) PGE2, ii) TGFβ, iii) rapamycin, optionally iv) at least one cytokine selected in the group of IL-2 and IL-15, and optionally v) vitamin C, for at least 5 days,
  thereby obtaining a population of γδ Foxp3$^+$ regulatory T cells ex vivo generated, preferably from γδ naïve (CD45RA$^+$) T cells.

In one embodiment, the method for generating ex vivo γδ Foxp3$^+$ regulatory T cells, comprises:
  culturing CD3$^+$ TCR γδ$^+$ T cells, preferably CD3$^+$ TCR γδ$^+$ CD45RA$^+$ T cells, in the presence of tolerogenic DC that have been pulsed with zoledronate during about 24 h and in the presence of ΔCD3 feeder cells and in the presence of the following agents: i) PGE2, ii) TGFβ, iii) rapamycin, optionally iv) at least one cytokine selected in the group of IL-2 and IL-15, and optionally v) vitamin C, for at least 5 days,
  thereby obtaining a population of γδ Foxp3$^+$ regulatory T cells ex vivo generated, preferably from γδ naïve (CD45RA$^+$) T cells.

The present invention also relates to an ex vivo method of generation and expansion of γδ Foxp3$^+$ regulatory T cells, comprising:
  generating the γδ Foxp3$^+$ regulatory T cells as described here above,
  expanding the γδ Foxp3$^+$ regulatory T cells generated by contacting them in the presence of an γδ T cell activator (preferably either autologous ΔCD3 feeder cells and coated anti-TCR γδ antibody or tolerogenic DC that have been pulsed with zoledronate during about 24 h and in the presence of ΔCD3 feeder cells) and the following agents: i) an cAMP (Cyclic adenosine monophosphate) activator (preferably PGE2), ii) a TGFβ (Transforming growth factor beta) pathway activator (preferably TGFβ), iii) a mTOR inhibitor (preferably rapamycin), optionally iv) at least one cytokine selected in the group of IL-2, IL-7, IL-15 and TSLP (preferably IL-2 and/or IL-15), and optionally v) at least one TET enzymes activator (preferably selected from vitamin C and a NaHS hydrogen sulfide releasing agent) and/or at least one DNMT inhibitor (such as, for example, RG108, DAC or 5AC), for at least 5 days,
  thereby obtaining an expanded population of γδ Foxp3$^+$ regulatory T cells.

In one embodiment, the γδ Foxp3$^+$ regulatory T cell population generated ex vivo is isolated by flow cytometry based on the following phenotype: CD3$^+$TCR γδ$^+$ CD45RO$^+$Foxp3$^+$.

In one embodiment, the isolated γδ Foxp3$^+$ regulatory T cell population thus obtained is then expanded ex vivo by culturing these cells in the presence of a polyclonal γδ T cell activator. Examples of polyclonal γδ T cell activator are listed hereinabove. Alternatively, other examples of polyclonal T cell activators that may be used during expansion include, but are not limited to, mitogen such as PMA/ionomycin, super-antigen, anti-CD3 antibody . . . . Preferably, the anti-CD3 monoclonal antibody is coated. In one embodiment, the polyclonal γδ T cell activator can be used in the presence of feeder cells as described here above.

In another embodiment, the isolated γδ Foxp3$^+$ regulatory T cell population thus obtained is then expanded ex vivo by culturing these cells in the presence of antigen-specific γδ cell activator as described here above. In one embodiment, the antigen-specific γδ T cell activator can be used in the presence of feeder cells as described here above.

In one embodiment, the culture for expanding the ex vivo generated γδ Foxp3$^+$ regulatory T cells of the invention is performed during at least 5 days, at least 6 days, at least 7 days, at least 8 days. Within the scope of the invention, the expression "at least 5 days" includes, without limitation, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days or more.

In one embodiment, a portion of the culture medium is discarded once, twice, three times, four times or five times during the time course of the generation culture and replaced with the same volume of fresh culture medium. Within the scope of the invention the term "portion" is intended to mean at least 20% (v/v), at least 25% (v/v), at least 30% (v/v), at least 35% (v/v), at least 40% (v/v), at least 45% (v/v), at least 50% (v/v), at least 55% (v/v), at least 60% (v/v), at least 65% (v/v), at least 70% (v/v), at least 75% (v/v) of the volume of the culture medium. In certain embodiments, 40% (v/v) to 60% (v/v) of the volume of the culture medium of step a) is discarded. In certain embodiments, the volume that is discarded is replaced with an identical volume of fresh culture medium. Within the scope of the invention, the expression "fresh culture medium" refers to a culture medium that has not been in contact with any CD3+ T cells.

In one embodiment, γδ Foxp3+ regulatory T cells are generated ex vivo by culturing CD3+TCR γδ+ CD45RA+ T cells obtained from PBMCs by flow cytometry ($5.10^3$ cells/ml) in the presence of autologous ΔCD3 feeder cells ($125\ 10^5$ cells/ml) and coated anti-TCR γδ antibody (2 μg/ml) in the presence of PGE2 (1 μM), TGFβ (5 ng/ml), Rapamycin (10 nM) and IL-2 (100 UI/ml) in IMDM-5. On day 1, IL-2 (100 UI/ml) and IL-15 (10 ng/ml) are added to the culture. Every 3 days, half of the medium volume is discarded and replaced by fresh medium comprising PGE2 (50 nM), TGFβ (5 ng/ml), Rapamycin (1 nM), IL-2 (100 UI/ml) and IL-15 (10 ng/ml). Once cells begin to expand, they can be split every 2 or 3 days and cultured in the presence of ΔCD3 feeder cells and coated anti-TCR γδ antibody every 9 days in a medium comprising PGE2 (1 μM), TGFβ (5 ng/ml), Rapamycin (10 nM) and IL-2 (100 UI/ml).

In another embodiment, γδ Foxp3+ regulatory T cells are generated ex vivo by culturing CD3+ TCR γδ+ CD45RA+ T cells ($5.10^3$ cells/ml) obtained from PBMCs by flow cytometry ($5.10^3$ cells/ml) in the presence of tolerogenic DCs, that have been pulsed with zoledronate during about 24 h, and in the presence of ΔCD3 feeder cells ($125\ 10^5$ cells/ml), PGE2 (1 μM), TGFβ (5 ng/ml), Rapamycin (10 nM) and IL-2 (100 UI/ml) in IMDM-5. On day 1, IL-2 (100 UI/ml), IL-15 (10 ng/ml) and TGFβ (5 ng/ml), are added to the culture. Every 3 days, half of the medium volume is discarded and replaced by fresh medium comprising PGE2 (50 nM), TGFβ (5 ng/ml), Rapamycin (1 nM), IL-2 (100 UI/ml) and IL-15 (10 ng/ml). Once cells begin to expand, they can be split every 2 or 3 days and restimulated every 9 days with tolerogenic DCs in the presence of ΔCD3 feeder cells and PGE2 (1 μM), TGFβ (5 ng/ml), Rapamycin (10 nM) and IL-2 (100 UI/ml).

In this embodiment, tolerogenic DCs were obtained by culturing CD14+ monocytes isolated from PBMCs in the presence of AIMV supplemented with GMCSF (100 ng/ml) and IL-4 (10 ng/ml). At day 3 and 6, the medium is discarded and replaced by fresh medium comprising GM-CSF and IL-4. On day 6, the tolerogenic DCs are pulsed for 24 hours in the presence of zoledronate (100 nM).

The present invention also relates to γδ Foxp3+ regulatory T cells obtainable by the ex vivo generation method as described here above.

The present invention also relates to γδ Foxp3+ regulatory T cells obtainable by the ex vivo generation and expansion method as described here above.

In one embodiment, the population of γδ Foxp3+ regulatory T cells obtained by the generation and expansion method of the invention comprises at least $10^6, 10^7, 10^8, 10^9, 10^{10}$ cells.

In one embodiment, the population of γδ Foxp3+ regulatory T cells obtained by the generation and expansion method of the invention has the following phenotype: CD3+ TCR γδ+ Foxp3+.

In one embodiment, the γδ Foxp3+ regulatory T cells obtainable or obtained by the method of the invention express the Vδ2 isotype. In one embodiment, the γδ Foxp3+ regulatory T cells of the invention do not express the Vδ2 isotype In another embodiment, the γδ Foxp3+ regulatory T cells obtainable or obtained by the method of the invention express the Vγ9 isotype. In one embodiment, the γδ Foxp3+ regulatory T cells of the invention do not express the Vγ9 isotype.

In one embodiment, the γδ Foxp3+ regulatory T cells obtainable or obtained by the method of the invention express the Vγ9Vδ2 isotype. In one embodiment, the γδ Foxp3+ regulatory T cells of the invention do not express the Vγ9Vδ2 isotype.

In one embodiment, the γδ Foxp3+ regulatory T cells of the invention express the Vδ3 isotype. In one embodiment, the γδ Foxp3+ regulatory T cells of the invention express the Vδ4 isotype. In one embodiment, the γδ Foxp3+ regulatory T cells of the invention express the Vδ5 isotype. In one embodiment, the γδ Foxp3+ regulatory T cells of the invention express the Vδ6 isotype.

In one embodiment, said population of γδ Foxp3+ regulatory T cells has the following phenotype: CD4+ Foxp3+ TCRγδ+.

In one embodiment, said population of γδ Foxp3+ regulatory T cells has the following phenotype: CD4+ Foxp3+ TCRγδ+CD25+.

In one embodiment, said population of γδ Foxp3+ regulatory T cells has the following phenotype: CD4+ Foxp3+ TCRγδ+ CTLA4+.

In one embodiment, said population of γδ Foxp3+ regulatory T cells has the following phenotype: CD4+ Foxp3+ TCRγδ+ CD45RO+.

In one embodiment, said population of γδ Foxp3+ regulatory T cells has the following phenotype: CD4+ Foxp3+ TCRγδ+ CD127+.

In one embodiment, said population of γδ Foxp3+ regulatory T cells has the following phenotype: CD4+ Foxp3+ TCRγδ+ IL-1R1−.

In one embodiment, said population of γδ Foxp3+ regulatory T cells has the following phenotype: CD4+ Foxp3+ TCRγδ+ IL-6R−.

In one embodiment, said population of γδ Foxp3+ regulatory T cells has the following phenotype: CD4+ Foxp3+ TCRγδ+ IL-23R−.

In one embodiment, said population of γδ Foxp3+ regulatory T cells has the following phenotype: CD4+ Foxp3+ TCRγδ+ IL-33R−.

In one embodiment, said population of γδ Foxp3+ regulatory T cells has the following phenotype: CD4+ Foxp3+ TCRγδ+ CD25+ CTLA4+.

In one embodiment, said population of γδ Foxp3+ regulatory T cells has the following phenotype: CD4+ Foxp3+ TCRγδ+ CD25+ CD45RO+.

In one embodiment, said population of γδ Foxp3+ regulatory T cells has the following phenotype: CD4+ Foxp3+ TCRγδ+ CD25+ CD127+.

In one embodiment, said population of γδ Foxp3+ regulatory T cells has the following phenotype: CD4+ Foxp3+ TCRγδ+ CTLA4+ CD45RO+.

In one embodiment, said population of γδ Foxp3+ regulatory T cells has the following phenotype: CD4+ Foxp3+ TCRγδ+ CTLA4+ CD127+.

In one embodiment, said population of γδ Foxp3+ regulatory T cells has the following phenotype: CD4+ Foxp3+ TCRγδ+ CD45RO+ CD127+.

In one embodiment, said population of γδ Foxp3+ regulatory T cells has the following phenotype: CD4+ Foxp3+ TCRγδ+ CD25+ IL-1R1−.

In one embodiment, said population of γδ Foxp3+ regulatory T cells has the following phenotype: CD4+ Foxp3+ TCRγδ+ CD25+ IL-6R−.

In one embodiment, said population of γδ Foxp3+ regulatory T cells has the following phenotype: CD4+ Foxp3+ TCRγδ+ CD25+ IL-23R−.

In one embodiment, said population of γδ Foxp3+ regulatory T cells has the following phenotype: CD4+ Foxp3+ TCRγδ+ CD25+ IL-33R−.

In one embodiment, said population of γδ Foxp3+ regulatory T cells has the following phenotype: CD4+ Foxp3+ TCRγδ+ CD25+ CTLA4+ CD45RO+.

In one embodiment, said population of γδ Foxp3+ regulatory T cells has the following phenotype: CD4+ Foxp3+ TCRγδ+ CD25+ CTLA4+ CD127+.

In one embodiment, said population of γδ Foxp3+ regulatory T cells has the following phenotype: CD4+ Foxp3+ TCRγδ+ CD25+ CD45RO+ CD127+.

In one embodiment, said population of γδ Foxp3+ regulatory T cells has the following phenotype: CD4+ Foxp3+ TCRγδ+ CTLA4+ CD45RO+ CD127+.

In one embodiment, said population of γδ Foxp3+ regulatory T cells has the following phenotype: CD4+ Foxp3+ TCRγδ+ IL-1R1− CTLA4+.

In one embodiment, said population of γδ Foxp3+ regulatory T cells has the following phenotype: CD4+ Foxp3+ TCRγδ+ IL-6R− CTLA4+.

In one embodiment, said population of γδ Foxp3+ regulatory T cells has the following phenotype: CD4+ Foxp3+ TCRγδ+ IL-23R− CTLA4+.

In one embodiment, said population of γδ Foxp3+ regulatory T cells has the following phenotype: CD4+ Foxp3+ TCRγδ+ IL-33R− CTLA4+.

In one embodiment, said population of γδ Foxp3+ regulatory T cells has the following phenotype: CD4+ Foxp3+ TCRγδ+ IL-1R1− CD127+.

In one embodiment, said population of γδ Foxp3+ regulatory T cells has the following phenotype: CD4+ Foxp3+ TCRγδ+ IL-6R− CD127+.

In one embodiment, said population of γδ Foxp3+ regulatory T cells has the following phenotype: CD4+ Foxp3+ TCRγδ+ IL-23R− CD127+.

In one embodiment, said population of γδ Foxp3+ regulatory T cells has the following phenotype: CD4+ Foxp3+ TCRγδ+ IL-33R− CD127+.

In one embodiment, said population of γδ Foxp3+ regulatory T cells has the following phenotype: CD4+ Foxp3+ TCRγδ+ IL-1R1− CD45RO+.

In one embodiment, said population of γδ Foxp3+ regulatory T cells has the following phenotype: CD4+ Foxp3+ TCRγδ+ IL-6R− CD45RO+.

In one embodiment, said population of γδ Foxp3+ regulatory T cells has the following phenotype: CD4+ Foxp3+ TCRγδ+ IL-23R− CD45RO+.

In one embodiment, said population of γδ Foxp3+ regulatory T cells has the following phenotype: CD4+ Foxp3+ TCRγδ+ IL-33R− CD45RO+.

In one embodiment, said population of γδ Foxp3+ regulatory T cells has the following phenotype: CD4+ Foxp3+ TCRγδ+ IL-1R1− IL-6R−.

In one embodiment, said population of γδ Foxp3+ regulatory T cells has the following phenotype: CD4+ Foxp3+ TCRγδ+ IL-1R1− IL-23R−.

In one embodiment, said population of γδ Foxp3+ regulatory T cells has the following phenotype: CD4+ Foxp3+ TCRγδ+ IL-1R1− IL-33R−.

In one embodiment, said population of γδ Foxp3+ regulatory T cells has the following phenotype: CD4+ Foxp3+ TCRγδ+ IL-6R− IL-23R−.

In one embodiment, said population of γδ Foxp3+ regulatory T cells has the following phenotype: CD4+ Foxp3+ TCRγδ+ IL-6R− IL-33R−.

In one embodiment, said population of γδ Foxp3+ regulatory T cells has the following phenotype: CD4+ Foxp3+ TCRγδ+ IL-23R− IL-33R−.

In one embodiment, said population of γδ Foxp3+ regulatory T cells has the following phenotype: CD4+ Foxp3+ TCRγδ+ CD25+ CTLA4+ CD45RO+ CD127+.

In one embodiment, said population of γδ Foxp3+ regulatory T cells has the following phenotype: CD4+ Foxp3+ TCRγδ+ CD25+ IL-1R1− CTLA4+.

In one embodiment, said population of γδ Foxp3+ regulatory T cells has the following phenotype: CD4+ Foxp3+ TCRγδ+ CD25+ IL-6R− CTLA4+.

In one embodiment, said population of γδ Foxp3+ regulatory T cells has the following phenotype: CD4+ Foxp3+ TCRγδ+ CD25+ IL-23R− CTLA4+.

In one embodiment, said population of γδ Foxp3+ regulatory T cells has the following phenotype: CD4+ Foxp3+ TCRγδ+ CD25+ IL-33R− CTLA4+.

In one embodiment, said population of γδ Foxp3+ regulatory T cells has the following phenotype: CD4+ Foxp3+ TCRγδ+ CD25+ IL-1R1− CD127+.

In one embodiment, said population of γδ Foxp3+ regulatory T cells has the following phenotype: CD4+ Foxp3+ TCRγδ+ CD25+ IL-6R− CD127+.

In one embodiment, said population of γδ Foxp3+ regulatory T cells has the following phenotype: CD4+ Foxp3+ TCRγδ+ CD25+ IL-23R− CD127+.

In one embodiment, said population of γδ Foxp3+ regulatory T cells has the following phenotype: CD4+ Foxp3+ TCRγδ+ CD25+ IL-33R− CD127+.

In one embodiment, said population of γδ Foxp3+ regulatory T cells has the following phenotype: CD4+ Foxp3+ TCRγδ+ CD25+ IL-1R1− CD45RO+.

In one embodiment, said population of γδ Foxp3+ regulatory T cells has the following phenotype: CD4+ Foxp3+ TCRγδ+ CD25+ IL-6R− CD45RO+.

In one embodiment, said population of γδ Foxp3+ regulatory T cells has the following phenotype: CD4+ Foxp3+ TCRγδ+ CD25+ IL-23R− CD45RO+.

In one embodiment, said population of γδ Foxp3+ regulatory T cells has the following phenotype: CD4+ Foxp3+ TCRγδ+ CD25+ IL-33R− CD45RO+.

In one embodiment, said population of γδ Foxp3+ regulatory T cells has the following phenotype: CD4+ Foxp3+ TCRγδ+ CD25+ IL-1R1− IL-6R−.

In one embodiment, said population of γδ Foxp3+ regulatory T cells has the following phenotype: CD4+ Foxp3+ TCRγδ+ CD25+ IL-1R1− IL-23R−.

In one embodiment, said population of γδ Foxp3+ regulatory T cells has the following phenotype: CD4+ Foxp3+ TCRγδ+ CD25+ IL-1R1− IL-33R−.

In one embodiment, said population of γδ Foxp3+ regulatory T cells has the following phenotype: CD4+ Foxp3+ TCRγδ+ CD25+ IL-6R− IL-23R−.

In one embodiment, said population of γδ Foxp3+ regulatory T cells has the following phenotype: CD4+ Foxp3+ TCRγδ+ CD25+ IL-6R− IL-33R−.

In one embodiment, said population of γδ Foxp3+ regulatory T cells has the following phenotype: CD4+ Foxp3+ TCRγδ+ CD25+ IL-23R− IL-33R−.

In one embodiment, said population of γδ Foxp3+ regulatory T cells has the following phenotype: CD4+ Foxp3+ TCRγδ+ CTLA4+ CD45RO+ CD127+ IL-1R1−.

In one embodiment, said population of γδ Foxp3+ regulatory T cells has the following phenotype: CD4+ Foxp3+ TCRγδ+ CTLA4+ CD45RO+ CD127+ IL-6R−.

In one embodiment, said population of γδ Foxp3+ regulatory T cells has the following phenotype: CD4+ Foxp3+ TCRγδ+ CTLA4+ CD45RO+ CD127+ IL-23R−.

In one embodiment, said population of γδ Foxp3⁺ regulatory T cells has the following phenotype: CD4⁺ Foxp3⁺ TCRγδ⁺ CTLA4⁺ CD45RO⁺ CD127⁺ IL-33R⁻.

In one embodiment, said population of γδ Foxp3⁺ regulatory T cells has the following phenotype: CD4⁺ Foxp3⁺ TCRγδ⁺ CTLA4⁺ CD45RO⁺ CD127⁺ IL-1R1⁻ IL-6R⁻.

In one embodiment, said population of γδ Foxp3⁺ regulatory T cells has the following phenotype: CD4⁺ Foxp3⁺ TCRγδ⁺ CTLA4⁺ CD45RO⁺ CD127⁺ IL-1R1⁻ IL-23R⁻.

In one embodiment, said population of γδ Foxp3⁺ regulatory T cells has the following phenotype: CD4⁺ Foxp3⁺ TCRγδ⁺ CTLA4⁺ CD45RO⁺ CD127⁺ IL-1R1⁻ IL-33R⁻.

In one embodiment, said population of γδ Foxp3⁺ regulatory T cells has the following phenotype: CD4⁺ Foxp3⁺ TCRγδ⁺ CTLA4⁺ CD45RO⁺ CD127⁺ IL-6R⁻ IL-23R⁻.

In one embodiment, said population of γδ Foxp3⁺ regulatory T cells has the following phenotype: CD4⁺ Foxp3⁺ TCRγδ⁺ CTLA4⁺ CD45RO⁺ CD127⁺ IL-6R⁻ IL-33R⁻.

In one embodiment, said population of γδ Foxp3⁺ regulatory T cells has the following phenotype: CD4⁺ Foxp3⁺ TCRγδ⁺ CTLA4⁺ CD45RO⁺ CD127⁺ IL-23R⁻ IL-33R⁻.

In one embodiment, said population of γδ Foxp3⁺ regulatory T cells has the following phenotype: CD4⁺ Foxp3⁺ TCRγδ⁺ CTLA4⁺ CD45RO⁺ CD127⁺ IL-6R⁻ IL-23R⁻ IL-33R⁻.

In one embodiment, said population of γδ Foxp3⁺ regulatory T cells has the following phenotype: CD4⁺ Foxp3⁺ TCRγδ⁺ CTLA4⁺ CD45RO⁺ CD127⁺ IL-1R1⁻ IL-23R⁻ IL-33R⁻.

In one embodiment, said population of γδ Foxp3⁺ regulatory T cells has the following phenotype: CD4⁺ Foxp3⁺ TCRγδ⁺ CTLA4⁺ CD45RO⁺ CD127⁺ IL-1R1⁻ IL-6R⁻ IL-33R⁻.

In one embodiment, said population of γδ Foxp3⁺ regulatory T cells has the following phenotype: CD4⁺ Foxp3⁺ TCRγδ⁺ CTLA4⁺ CD45RO⁺ CD127⁺ IL-1R1⁻ IL-6R⁻ IL-23R⁻.

In one embodiment, said population of γδ Foxp3⁺ regulatory T cells has the following phenotype: CD4⁺ Foxp3⁺ TCRγδ⁺ CTLA4⁺ CD45RO⁺ CD127⁺ IL-1R1⁻ IL-6R⁻ IL-23R⁻ IL-33R⁻.

In one embodiment, said population of γδ Foxp3⁺ regulatory T cells has the following phenotype: CD4⁺ Foxp3⁺ TCRγδ⁺ CD25⁺ CTLA4⁺ CD45RO⁺ CD127⁺ IL-1R1⁻.

In one embodiment, said population of γδ Foxp3⁺ regulatory T cells has the following phenotype: CD4⁺ Foxp3⁺ TCRγδ⁺ CD25⁺ CTLA4⁺ CD45RO⁺ CD127⁺ IL-6R⁻.

In one embodiment, said population of γδ Foxp3⁺ regulatory T cells has the following phenotype: CD4⁺ Foxp3⁺ TCRγδ⁺ CD25⁺ CTLA4⁺ CD45RO⁺ CD127⁺ IL-23R⁻.

In one embodiment, said population of γδ Foxp3⁺ regulatory T cells has the following phenotype: CD4⁺ Foxp3⁺ TCRγδ⁺ CD25⁺ CTLA4⁺ CD45RO⁺ CD127⁺ IL-33R⁻.

In one embodiment, said population of γδ Foxp3⁺ regulatory T cells has the following phenotype: CD4⁺ Foxp3⁺ TCRγδ⁺ CD25⁺ CTLA4⁺ CD45RO⁺ CD127⁺ IL-1R1⁻ IL-6R⁻.

In one embodiment, said population of γδ Foxp3⁺ regulatory T cells has the following phenotype: CD4⁺ Foxp3⁺ TCRγδ⁺ CD25⁺ CTLA4⁺ CD45RO⁺ CD127⁺ IL-1R1⁻ IL-23R⁻.

In one embodiment, said population of γδ Foxp3⁺ regulatory T cells has the following phenotype: CD4⁺ Foxp3⁺ TCRγδ⁺ CD25⁺ CTLA4⁺ CD45RO⁺ CD127⁺ IL-1R1⁻ IL-33R⁻.

In one embodiment, said population of γδ Foxp3⁺ regulatory T cells has the following phenotype: CD4⁺ Foxp3⁺ TCRγδ⁺ CD25⁺ CTLA4⁺ CD45RO⁺ CD127⁺ IL-6R⁻ IL-23R⁻.

In one embodiment, said population of γδ Foxp3⁺ regulatory T cells has the following phenotype: CD4⁺ Foxp3⁺ TCRγδ⁺ CD25⁺ CTLA4⁺ CD45RO⁺ CD127⁺ IL-6R⁻ IL-33R⁻.

In one embodiment, said population of γδ Foxp3⁺ regulatory T cells has the following phenotype: CD4⁺ Foxp3⁺ TCRγδ⁺ CD25⁺ CTLA4⁺ CD45RO⁺ CD127⁺ IL-23R⁻ IL-33R⁻.

In one embodiment, said population of γδ Foxp3⁺ regulatory T cells has the following phenotype: CD4⁺ Foxp3⁺ TCRγδ⁺ CD25⁺ CTLA4⁺ CD45RO⁺ CD127⁺ IL-6R⁻ IL-23R⁻ IL-33R⁻.

In one embodiment, said population of γδ Foxp3⁺ regulatory T cells has the following phenotype: CD4⁺ Foxp3⁺ TCRγδ⁺ CD25⁺ CTLA4⁺ CD45RO⁺ CD127⁺ IL-1R1⁻ IL-23R⁻ IL-33R⁻.

In one embodiment, said population of γδ Foxp3⁺ regulatory T cells has the following phenotype: CD4⁺ Foxp3⁻ CD25⁺ CTLA4⁺ CD45RO⁺ CD127⁺ IL-1R1⁻ IL-6R⁻ IL-33R⁻.

In one embodiment, said population of γδ Foxp3⁺ regulatory T cells has the following phenotype: CD4⁺ Foxp3⁺ TCRγδ⁺ CD25⁺ CTLA4⁺ CD45RO⁺ CD127⁺ IL-1R1⁻ IL-6R⁻ IL-23R⁻.

In one embodiment, said population of γδ Foxp3⁺ regulatory T cells has the following phenotype: CD4⁺ Foxp3⁺ TCRγδ⁺ CD25⁺ CTLA4⁺ CD45RO⁺ CD127⁺ IL-1R1⁻ IL-6R⁻ IL-23R⁻ IL-33R⁻.

In one embodiment, the γδ Foxp3⁺ regulatory T cells of the invention do not present a regulatory T cells specific demethylated region (TSDR) of the gene Foxp3. In another embodiment, the γδ Foxp3⁺ regulatory T cells of the invention present a regulatory T cells specific demethylated region (TSDR) of the gene Foxp3. In one embodiment, the γδ Foxp3⁺ regulatory T cells present a percentage of demethylation of the TSDR of the gene FOXP3 superior to at least 30%, 40%, 50%. A protocol for measuring promoter demethylation percentage is shown in the Material and Method part of the Examples.

In another embodiment, the γδ Foxp3⁺ regulatory T cells present a percentage of enrichment of acetylated histone in Foxp3 promoter region superior to at least 10%, 20%, 30%, 40% or 50%. A protocol for measuring enrichment of acetylated histones in percentage is shown in the Material and Method part of the Examples.

An example of phenotypic characteristics of the population of γδ Foxp3⁺ regulatory T cells of the invention is shown in FIG. 1.

In one embodiment, said population of γδ Foxp3⁺ regulatory T cells express Foxp3 with a median fluorescence intensity (MFI) at least equivalent to the Foxp3 MFI measured in naïve regulatory T cells. As used herein, "naïve regulatory T cells" refer to T cells having for phenotype Foxp3⁺CD45RA⁺CD4⁺CD25⁺CD127⁻.

In one embodiment, the γδ Foxp3⁺ regulatory T cells express Foxp3 with a median fluorescence intensity (MFI) of at least 2000.

In one embodiment, the γδ Foxp3⁺ regulatory T cells express Foxp3 with a median fluorescence intensity (MFI) of at least 2 or 3 fold the Foxp3 MFI measured in naïve regulatory T cells.

In one embodiment, the γδ regulatory T cells express Foxp3 with a median fluorescence intensity (MFI) of at least 2000, 3000, 4000, 5000, 10000, 20000, 30000, 40000, 50000, 60000, 70000.

In one embodiment, the γδ Foxp3$^+$ regulatory T cells population comprises at least 65% of the CD3$^+$ CD4$^+$ cells expressing Foxp3. The expression "at least 65%" includes, without limitation, 65%, 66%, 67%, 68%, 69%, 70%, 71%, 72%, 73%, 74%, 752%, 76%, 77%, 78%, 79%, 80%, 81%, 82%, 83%, 84%, 85%, 86%, 87%, 88%, 89%, 90%, 91%, 82%, 93%, 94%, 95%, 96%, 97%, 98%, 99% and 100%.

As used herein, the term "expression" may refer alternatively to the transcription of a molecule (i.e. expression of the mRNA) or to the translation (i.e. expression of the protein) of a molecule. In one embodiment, detecting the expression may correspond to an intracellular detection. In another embodiment, detecting the expression may correspond to a surface detection, i.e. to the detection of molecule expressed at the cell surface. In another embodiment, detecting the expression may correspond to an extracellular detection, i.e. to the detection of secretion. In another embodiment, detecting the expression may correspond to intracellular, surface and/or extracellular detections. Methods for determining the expression level are well-known from the skilled artisan, and include, without limitation, determining the transcriptome (in an embodiment wherein expression relates to transcription of a molecule) or proteome (in an embodiment wherein expression relates to translation of a cytotoxic molecule) of cells.

In one embodiment of the invention, the expression of the molecules is assessed at the mRNA level. Methods for assessing the transcription level of a molecule are well known in the prior art. Examples of such methods include, but are not limited to, RT-PCR, RT-qPCR, Northern Blot, hybridization techniques such as, for example, use of microarrays, and combination thereof including but not limited to, hybridization of amplicons obtained by RT-PCR, sequencing such as, for example, next-generation DNA sequencing (NGS) or RNA-seq (also known as "Whole Transcriptome Shotgun Sequencing") and the like. In another embodiment of the invention, the expression of the molecules is assessed at the protein level. Methods for determining a protein level in a sample are well-known in the art. Examples of such methods include, but are not limited to, immunohistochemistry, Multiplex methods (Luminex), western blot, enzyme-linked immunosorbent assay (ELISA), sandwich ELISA, fluorescent-linked immunosorbent assay (FLISA), enzyme immunoassay (EIA), radioimmunoassay (RIA), flow cytometry (FACS) and the like.

In another embodiment, determining the expression level of at least one molecule corresponds to detecting and/or quantifying binding of a ligand to a molecule. In one embodiment, said ligand is an antibody specific of said molecule, and the method of the invention comprises detecting and/or quantifying a complex formed between said antibody and said molecule. The complex can be detected if the ligand has been for example, but not limited to, covalently coupled with a detectable molecule such as an antibody constant fragment (Fc) or a fluorescent compound (e.g. Cyanine dye, Alexa dye, Quantum dye, etc.). The complex can also be detected if the ligand has been tagged with different means well known to the person skilled in the art. For example, but without limitation, a tag used with the invention can be a tag selected from the group comprising or consisting of Hemaglutinin Tag, Poly Arginine Tag, Poly Histidine Tag, Myc Tag, Strep Tag, S-Tag, HAT Tag, 3× Flag Tag, Calmodulin-binding peptide Tag, SBP Tag, Chitin binding domain Tag, GST Tag, Maltose-Binding protein Tag, Fluorescent Protein Tag, T7 Tag, V5 Tag and Xpress Tag. The use of the ligand therefore allows on the one hand the identification and detection of the molecule depending on the ligand used, and on the other hand the quantification of the complex formed.

In one embodiment, determining the expression level of molecules is conducted by flow cytometry, immunofluorescence or image analysis, for example high content analysis. Preferably, the determination of the expression level of molecules is conducted by flow cytometry. In one embodiment, before conducting flow cytometry analysis, cells are fixed and permeabilized, thereby allowing detecting intracellular proteins.

In one embodiment, determining the expression level of a molecule in a cell population comprises determining the percentage of cells of the cell population expressing the molecule (i.e. cells "+" for the molecule). Preferably, said percentage of cells expressing the molecule is measured by FACS.

The terms "expressing (or +)" and "not expressing (or −)" are well known in the art and refer to the expression level of the cell marker of interest, in that the expression level of the cell marker corresponding to "+" is high or intermediate, also referred as "+/−". The cell marker corresponding to "−" is a null expression level of the cell marker or also refers to less than 10% of a cell population expressing the said cell marker.

The expression level of the cell marker of interest is determined by comparing the Median Fluorescence Intensity (MFI) of the cells from the cell population stained with fluorescently labeled antibody specific for this marker to the Fluorescence Intensity (FI) of the cells from the same cell population stained with fluorescently labeled antibody with an irrelevant specificity but with the same isotype, the same fluorescent probe and originated from the same specie (referred as Isotype control). The cells from the population stained with fluorescently labeled antibody specific for this marker and that show equivalent MFI or a lower MFI than the cells stained with the isotype controls are not expressing this marker and then are designated (−) or negative. The cells from the population stained with fluorescently labeled antibody specific for this marker and that show a MFI value superior to the cells stained with the isotype controls are expressing this marker and then are designated (+) or positive.

In one embodiment, the γδ Foxp3$^+$ regulatory T cells are capable of suppressive activity similar to the suppressive activity of naïve CD4$^+$ CD25$^+$ CD45RA$^+$ CD127$^-$ regulatory T cells. Determination of the suppressive activity of a cell population is well known in the art and can be performed by conventional assays such as the standard polyclonal cell-cell contact Treg suppression assay or the autologous MLR suppression assay as described in the Examples.

Another object of the invention is a population of γδ Foxp3$^+$ regulatory T cells that remains functionally stable when placed in inflammatory conditions.

In one embodiment, the population of γδ Foxp3$^+$ regulatory T cells obtainable or obtained by the ex vivo generation and expansion method of the invention has the property to remain functionally stable when placed in inflammatory conditions.

As used herein, "functionally stable" refers to no secretion or a low secretion of IL-17, i.e. inferior to 200 ng/ml, 100 ng/ml, 50 ng/ml and still capable of suppressive capacity, i.e. inhibiting proliferation of conventional T cells as shown in the Examples.

As used herein, "inflammatory condition" refers to a medium enriched in aromatic acid, preferably in tryptophan, such as for example IMDM, comprising inflammatory cytokines such as for example IL-1β (10 ng/ml), IL-6 (30 ng/ml), IL-21 (50 ng/ml), IL-23 (30 ng/ml), IL-2 (100 UI/ml). A method for determining if a population of regulatory T cells remains functionally stable in inflammatory condition comprises culturing the regulatory T cells in the inflammatory condition medium as described here above in the presence of anti-CD3 (4 µg/ml), preferably coated, and anti-CD28 (4 µg/ml), preferably in a soluble form. After 36 h to 72 h of culture, the presence of IL-17 in the culture supernatant is measured. The recognition of IL-17 in the culture supernatant may be carried out by conventional methods known in the art such as, for example, a sandwich ELISA anti-IL-17. Briefly, after coated the plate with a capture anti-IL-17 antibody, the culture supernatant is added to each well with a dilution series. After incubation, a detection anti-IL-17 antibody is added to each well. The ELISA is developed by any colorimetric means known in the art such as, for example, using detection antibody labelled with biotin, a poly-streptavidin HRP amplification system and an o-phenylenediamine dihydrochloride substrate solution. An IL-17 level inferior to 200 ng/ml, 100 ng/ml, 50 ng/ml corresponds to no secretion or low secretion of IL-17.

Without wishing to be bound to a theory, the inventors state that the stroma of malignant tumor cells comprises TILs (Tumor-infiltrating lymphocytes) that are highly enriched in regulatory T cells and that exert an immune suppressive activity, in particular on NK cells, which likely accounts on the local cancer immune escape. The inactivated γδ Foxp3$^+$ regulatory T cells may represent an antigenic target to induce an immune response directed against the γδ Foxp3$^+$ regulatory T cells present in the TILs, thereby preventing their immune suppressive activity and allowing the cytotoxic activity of effector cells such as NK cells against the tumor cells. The inventors thus suggest using a vaccine composition comprising inactivated γδ Foxp3$^+$ regulatory T cells as active principle.

One object of the invention is an immunogenic product comprising, consisting essentially of or consisting of inactivated γδ Foxp3$^+$ regulatory T cells as described here above.

In one embodiment, the immunogenic product comprises, consists essentially of or consists of inactivated γδ Foxp3$^+$ regulatory T cells having the following phenotype CD3$^+$ TCR γδ$^+$ Foxp3$^+$ as described here above.

As used herein, the term "consisting essentially of", with reference to an immunogenic product, pharmaceutical composition, vaccine or medicament, means that the at least one γδ Foxp3$^+$ regulatory T cell population or antibody of the invention is the only one therapeutic agent or agent with a biologic activity within said immunogenic product, pharmaceutical composition, vaccine or medicament.

In one embodiment, the immunogenic product comprises, consists essentially of or consists of inactivated γδ Foxp3$^+$ regulatory T cells having the following phenotype CD3$^+$ TCR γδ$^+$ Foxp3$^+$ generated and optionally expanded ex vivo by the method as described here above.

One object of the invention is an immunogenic product comprising blebs from γδ Foxp3$^+$ regulatory T cells as described here above.

One object of the invention is an immunogenic product comprising immunogenic dendritic cells (immunogenic DC) loaded with blebs from γδ Foxp3$^+$ regulatory T cells as described here above.

As used herein, "immunogenic DCs" refers to DCs capable to induce an immunogenic response. In one embodiment, immunogenic DCs have the following phenotype: CD80$^{high}$ CD83$^{high}$ CD86$^{high}$ HLA class I$^{high}$ and HLA class II$^{high}$ and secrete IL-10 and IL-12 with a ratio IL-12/IL-10>1.

Methods for obtaining immunogenic DCs are well-known in the art. An exemplary method the generation of immunogenic DCs from CD14$^+$ monocytes. For example, CD14$^+$ monocytes are cultured in the presence of GM-CSF (about 20 ng/mL) and IFNα (about 10 ng/mL) for obtaining MoDC. Maturation of MoDC may be induced by a cytokine cocktail consisting of IL-1β (about 10 ng/ml), IL-6 (about 10 ng/ml) TNFα (about 200 U/ml), and PGE2 (about 10 ng/ml).

Another object of the invention is a pharmaceutical composition comprising, consisting essentially of or consisting of the immunogenic product as described here above and at least one pharmaceutically acceptable excipient.

Another object of the invention is a pharmaceutical composition comprising, consisting essentially of or consisting of inactivated γδ Foxp3$^+$ regulatory T cells having the following phenotype CD3$^+$ TCR γδ$^+$ Foxp3$^+$ and at least one pharmaceutically acceptable excipient.

Another object of the invention is a pharmaceutical composition comprising, consisting essentially of or consisting of inactivated γδ Foxp3$^+$ regulatory T cells having the following phenotype CD3$^+$ TCR γδ$^+$ Foxp3$^+$ generated and expanded ex vivo by the method as described here above and at least one pharmaceutically acceptable excipient.

Another object of the invention is a pharmaceutical composition comprising, consisting essentially of or consisting of blebs of γδ Foxp3$^+$ regulatory T cells having the following phenotype CD3$^+$ TCR γδ$^+$ Foxp3$^+$ as described here above and at least one pharmaceutically acceptable excipient.

Another object of the invention is a pharmaceutical composition comprising, consisting essentially of or consisting of immunogenic DC loaded with blebs of γδ Foxp3$^+$ regulatory T cells having the following phenotype CD3$^+$ TCR γδ$^+$ Foxp3$^+$ as described here above and at least one pharmaceutically acceptable excipient.

As used herein, the term "excipient" refers to any and all conventional solvents, dispersion media, fillers, solid carriers, aqueous solutions, coatings, antibacterial and antifungal agents, isotonic and absorption delaying agents and the like. For human administration, preparations should meet sterility, pyrogenicity, general safety and purity standards as required by regulatory offices, such as, for example, FDA Office or EMA.

By "pharmaceutically acceptable" is meant that the ingredients of a pharmaceutical composition are compatible with each other and not deleterious to the subject to which it is administered. Examples of pharmaceutically acceptable excipient include, but are not limited to, water, saline, phosphate buffered saline, dextrose, glycerol, ethanol and the like or combinations thereof.

Another object of the invention is a vaccine composition comprising, consisting essentially of or consisting of the immunogenic product as described here above.

Another object of the invention is a vaccine composition comprising, consisting essentially of or consisting of inactivated γδ Foxp3$^+$ regulatory T cells having the following phenotype CD3$^+$ TCR γδ$^+$ Foxp3$^+$.

Another object of the invention is a vaccine composition comprising, consisting essentially of or consisting of inactivated γδ Foxp3$^+$ regulatory T cells having the following phenotype CD3$^+$ TCR γδ$^+$ Foxp3$^+$ generated and expanded ex vivo by the method as described here above.

Another object of the invention is a vaccine composition comprising, consisting essentially of or consisting of blebs of γδ Foxp3+ regulatory T cells having the following phenotype CD3+ TCR γδ+ Foxp3+ as described here above.

Another object of the invention is a vaccine composition comprising, consisting essentially of or consisting of immunogenic DC loaded with blebs of γδ Foxp3+ regulatory T cells having the following phenotype CD3+ TCR γδ+ Foxp3+ as described here above.

As used herein, "inactivated" T cells refers to T cells that are viable but has reduced or no effector function, i.e. have lost any pathogenic potential. Examples of cell surface markers of inactivated T cells include, but are not limited to, 7-Aminoactinomycin D (7-AAD), calreticulin and heat shock protein 90 (HSP-90). Therefore, inactivated T cells express 7-AAD and/or calreticulin and/or HSP-90. The inactivated γδ Foxp3+ regulatory T cells of the invention have lost their suppressive activity but are still immunogenic. An example of T cell effector function assay is, but not limited to, T-cell proliferation assay. T-cell proliferation may be assessed on fixed T cells versus non-fixed T cells. Briefly, the T-cell proliferation assay aims at determining the percentage of living proliferating cells in fixed versus non-fixed T cells by flow cytometry. After staining the T cells with CFSE, anti-CD3 antibody and 7-AAD, the living proliferating cells are defined as the CFSE$^{low}$ fraction in gated CD3+ 7-AAD− cells.

In one embodiment, the γδ Foxp3+ regulatory T cells are inactivated by any method well-known in the art. Examples of method for inactivating cells include, but are not limited to, irradiation, preferably with about 2500 to 3000 rads and/or chemical inactivation such as exposure to cisplatin, carboplatin, oxaliplatin, mitomycine C or antracycline.

In one embodiment, the vaccine composition of the invention further comprises at least one adjuvant. Examples of adjuvant that can be used in the vaccine composition include, but are not limited to, ISA51; emulsions such as CFA, MF59, montanide, AS03 and AF03; mineral salts such as alum, calcium phosphate, iron salt, zirconium salt, and AS04; TLR ligands such as TLR2 ligands (such as outer-surface protein A or OspA), TLR3 ligands (such as poly I:C), TLR4 ligands (such as MPL and GLA), TLR5 ligands, TLR7/8 ligands (such as imiquimod), TLR9 ligands (such as CpG ODN); polysacharrides such as chitin, chitosan, α-glucans, β-glucans, fructans, mannans, dextrans, lentinans, inulin-based adjuvants (such as gamma inulin); TLR9 and STING ligands such as K3 CpG and cGAMP. As used herein, "adjuvant" refers to an agent that potentiates the immune responses to an antigen and/or modulates it towards the desired immune responses.

In one embodiment, the inactivated γδ Foxp3+ regulatory T cells are specific of at least one non-peptide phosphoantigen as described hereabove.

In another embodiment, the inactivated γδ Foxp3+ regulatory T cells are specific of at least one non-peptide phosphoantigen that were present on apoptotic bodies of cancer cells.

In another embodiment, the inactivated γδ Foxp3+ regulatory T cells are specific of at least one non-peptide phosphoantigen that were present on blebs of cancer cells.

In one embodiment, the inactivated γδ Foxp3+ regulatory T cells present in the immunogenic product, pharmaceutical composition or vaccine composition of the invention are human γδ Foxp3+ regulatory T cells.

In one embodiment, the inactivated γδ Foxp3+ regulatory T cells present in the immunogenic product, pharmaceutical composition or vaccine composition of the invention are autologous γδ Foxp3+ regulatory T cells.

In one embodiment, the inactivated γδ Foxp3+ regulatory T cells present in the immunogenic product, pharmaceutical composition or vaccine composition of the invention are allogenic γδ Foxp3+ regulatory T cells.

In another embodiment, the immunogenic product, pharmaceutical composition or vaccine composition of the invention may be personalized for a patient. As used herein, a "personalized" immunogenic product or vaccine composition refers to the use of γδ Foxp3+ regulatory T cells generated and expanded ex vivo with at least one patient specific epitope. In this embodiment, the γδ Foxp3+ regulatory T cells to be used as immunogenic product or in the vaccine composition are generated and expanded ex vivo in the presence of apoptotic bodies of cancer cells obtained from the patient or in the presence of blebs of cancer cells, thereby providing at least one patient specific epitope.

In one embodiment, the immunogenic product, pharmaceutical composition or vaccine composition of the invention comprises, consists essentially of or consists of inactivated γδ Foxp3+ regulatory T cells as active principle.

In one embodiment, the immunogenic product, pharmaceutical composition or vaccine composition of the invention comprises, consists essentially of or consists of at least $10^4$, $10^5$, $10^6$, $10^7$, $10^8$, $10^9$, $10^{10}$ inactivated γδ Foxp3+ regulatory T cells as active principle.

In one embodiment, the immunogenic product, pharmaceutical composition or vaccine composition of the invention comprises, consists essentially of or consists of about $10^4$, $5\times10^4$, $10^5$, $5\times10^5$, $10^6$, $5\times10^6$, $10^7$, $5\times10^7$, $10^8$, $5\times10^8$, $10^9$, $5\times10^9$, $10^{10}$, inactivated γδ Foxp3+ regulatory T cells as active principle.

In one embodiment, the γδ Foxp3+ regulatory T cells, the inactivated γδ Foxp3+ regulatory T cells, the immunogenic product, the pharmaceutical composition or the vaccine composition of the invention are/is frozen.

In one embodiment, the immunogenic product, pharmaceutical composition or vaccine composition of the invention may be administrated to the subject by subcutaneous, intramuscular, intraperitoneal or intravenous injection, or directly into the tumor.

In one embodiment, the immunogenic product, pharmaceutical composition or vaccine composition of the invention may be administrated to the subject at least once, twice, 3 times, 4 times, 5 times in a year. Example of regime of administration includes, but is not limited to, administration of the immunogenic product or vaccine composition at day 0, 4 weeks after day 0, 8 weeks after day 0, 12 weeks after day 0 and 24 weeks after day 0.

Another object of the invention is a method for treating cancer in a subject in need thereof, comprising administering to the subject a therapeutically effective amount of inactivated γδ Foxp3+ regulatory T cells or of the immunogenic product, pharmaceutical composition or vaccine composition of the invention as described here above.

Another object of the invention is a method for eliciting an immune response against γδ Foxp3+ regulatory T cells present in the TILs of a subject affected with a cancer, comprising administering to the subject a therapeutically effective amount of inactivated γδ Foxp3+ regulatory T cells or of the immunogenic product, pharmaceutical composition or vaccine composition of the invention as described here above.

Examples of cancer that can be treated with the immunogenic product, pharmaceutical composition or vaccine composition of the invention include, but are not limited to, adrenocortical carcinoma, anal cancer, bladder cancer, ependymoma, medulloblastoma, supratentorial primitive neuroectodermal, pineal tumors, hypothalamic glioma, breast cancer, carcinoid tumor, carcinoma, cervical cancer, colon cancer, endometrial cancer, esophageal cancer, extrahepatic bile duct cancer, ewings family of tumors (pnet), extracranial germ cell tumor, eye cancer, intraocular melanoma, gallbladder cancer, gastric cancer, germ cell tumor, extragonadal, gestational trophoblastic tumor, head and neck cancer, hypopharyngeal cancer, islet cell carcinoma, laryngeal cancer, leukemia, acute lymphoblastic leukemia, oral cavity cancer, liver cancer, lung cancer, small cell lymphoma, AIDS-related, lymphoma, central nervous system (primary) lymphoma, cutaneous T-cell lymphoma, Hodgkin's disease, non-Hodgkin's disease, malignant mesothelioma, melanoma, merkel cell carcinoma, metastatic squamous carcinoma, multiple myeloma, plasma cell neoplasms, mycosis fungoides, myelodysplastic syndrome, myeloproliferative disorders, nasopharyngeal cancer, neuroblastoma, oropharyngeal cancer, osteosarcoma, ovarian epithelial cancer, ovarian germ cell tumor, ovarian low malignant potential tumor, pancreatic cancer, exocrine, pancreatic cancer, paranasal sinus and nasal cavity cancer, parathyroid cancer, pheochromocytoma cancer, pituitary cancer, plasma cell neoplasm, rhabdomyosarcoma, rectal cancer, renal cell cancer, salivary gland cancer, Sezary syndrome, Kaposi's sarcoma, small intestine cancer, soft tissue sarcoma, thymoma, malignant thyroid cancer, urethral cancer, uterine cancer, sarcoma, unusual cancer of childhood, vaginal cancer, vulvar cancer or Wilms' tumor, benign conditions associated with chemotherapy treatments, such as, lupus, rheumatoid arthritis and skin diseases.

In one embodiment, the cancer that can be treated with the immunogenic product, pharmaceutical composition or vaccine composition of the invention include, but is not limited to, breast cancer, prostate cancer, ovarian cancer and glioblastoma.

Another object of the invention is a method for preparing the immunogenic product of the invention, comprising:
providing a biological sample, preferably a blood sample, from the subject to be treated and optionally a tumor sample, from the subject to be treated,
generating and expanding ex vivo as described here above γδ Foxp3$^+$ regulatory T cells from the CD3$^+$ TCRγδ$^+$ T cells, preferably CD3$^+$ TCRγδ$^+$CD45RA$^+$ T cells, isolated from the biological sample,
inactivating the γδ Foxp3$^+$ regulatory T cells obtained in the previous step,
thereby obtaining the immunogenic product of the invention.

In a preferred embodiment, the generation and expansion steps are carried out in the presence of tolerogenic dendritic cells (DCs), and pulsed with apoptotic tumor bodies or blebs obtained from the tumor sample of the subject.

Another object of the invention is a method for treating cancer in a subject in need thereof, comprising administrating to the subject the immunogenic product, pharmaceutical composition or vaccine composition of the invention.

Another object of the invention is a method for treating cancer in a subject in need thereof, comprising:
preparing an immunogenic product as described here above,
optionally preparing a pharmaceutical composition or a vaccine composition comprising the immunogenic product,
optionally submitting the subject to plasmapheresis,
administrating to the subject the immunogenic product, pharmaceutical composition or vaccine composition of the invention.

Without wishing to be bound by a theory, the inventors suggest that the γδ Foxp3$^+$ regulatory T cells of the invention, which are committed to exert immune suppressive function, may be capable of inhibiting autoreactive pathogenic immune effector cells including CD4$^+$, CD8$^+$, B cells or innate NK cells, which, in turn, are no longer able to exert their cytotoxic properties towards the self-cells.

One object of the invention is a pharmaceutical composition comprising, consisting essentially of or consisting of the γδ Foxp3$^+$ regulatory T cells or γδ Foxp3$^+$ regulatory T cell population as described here above and at least one pharmaceutically acceptable excipient.

Another object of the invention is a pharmaceutical composition comprising, consisting essentially of or consisting of γδ Foxp3$^+$ regulatory T cells having the following phenotype CD3$^+$ TCR γδ$^+$ Foxp3$^+$ and at least one pharmaceutically acceptable excipient.

Another object of the invention is a pharmaceutical composition comprising, consisting essentially of or consisting of γδ Foxp3$^+$ regulatory T cells having the following phenotype CD3$^+$ TCRγδ$^+$ Foxp3$^+$ generated and expanded ex vivo by the method as described here above and at least one pharmaceutically acceptable excipient.

One object of the invention is the γδ Foxp3$^+$ regulatory T cells or the γδ Foxp3$^+$ regulatory T cell population or the pharmaceutical composition as described here above for use in adoptive therapy.

Another object of the invention is the γδ Foxp3$^+$ regulatory T cells or the γδ Foxp3$^+$ regulatory T cell population or the pharmaceutical composition as described here above for use in treating inflammatory or autoimmune diseases.

Examples of inflammatory or autoimmune diseases include, but are not limited to, acute disseminated encephalomyelitis, acute necrotizing haemorrhagic leukoencephalitis, Addison's disease, agammaglobulinaemia, alopecia areata, amyloidosis, ankylosing spondylitis, anti-GBM/anti-TBM nephritis, antiphospholipid syndrome, autoimmune angioedema, autoimmune aplastic anaemia, autoimmune dysautonomia, autoimmune haemolytic anaemia, autoimmune hepatitis, autoimmune hyperlipidemia, autoimmune immunodeficiency, autoimmune inner ear disease, autoimmune myocarditis, autoimmune oophoritis, autoimmune pancreatitis, autoimmune retinopathy, autoimmune thrombocytopenic purpura, autoimmune thyroid disease, autoimmune urticaria, axonal and neuronal neuropathies, Balo disease, Behcet's disease, bullous pemphigoid, cardiomyopathy, Castleman disease, celiac disease, Chagas disease, chronic fatigue syndrome, chronic inflammatory demyelinating polyneuropathy, chronic recurrent multifocal osteomyelitis, Churg-Strauss syndrome, cicatricial pemphigoid/benign mucosal pemphigoid, Crohn's disease, Cogans' syndrome, cold agglutinin disease Congenital heart block, Coxsackie myocarditis, CREST disease, essential mixed cryoglobulinemia, demyelinating neuropathies, dermatitis herpetiformis, dermatomyositis, Devic's disease, discoid lupus, Dressler's syndrome, endometriosis, eosinophilic esophagitis, eosinophilic fasciitis, erythema nodosum, experimental allergic encephalomyelitis, Evans syndrome, fibromyalgia, fibrosing alveolitis, giant cell arteritis, giant cell myocarditis, glomerulonephritis, Goodpasture's syndrome, granulomatosis with Polyangiitis (Wegener's syndrome), Graves' disease, Guillain-Barre syndrome, Hashimoto's encephalitis, Hashimoto's thyroiditis, haemolytic anaemia, Henoch-Schonlein purpura, herpes gestationis, hypogammaglobulinemia, idiopathic pulmonary fibrosis, idiopathic thrombocytopenic purpura, IgA nephropathy, IgG4-related sclerosing disease, immunoregulatory lipoproteins, inclusion body myositis, interstitial cystitis, juvenile arthritis, juvenile diabetes (Type 1 diabetes), juvenile myositis, Kawasaki syndrome, Lambert-Eaton syndrome, leukocytoclastic vasculitis, lichen planus, lichen sclerosus, ligneous conjunctivitis, linear IgA disease, lupus, Lyme chronic disease, Meniere's disease, microscopic polyangiitis, mixed connective tissue disease, Mooren's ulcer, Mucha-Habermann disease, multiple sclerosis, myasthenia gravis, myositis, narcolepsy, neuromyelitis optica, neutropenia, ocular cicatricial pemphigoid, optic neuritis, palindromic rheumatism, paediatric autoimmune neuropsychiatric disorders associated with Streptococcus, paraneoplastic cerebellar degeneration, paroxysmal nocturnal hemoglobinuria, Parry Romberg syndrome, Parsonnage-Turner syndrome, pars planitis (peripheral uveitis), pemphigus, peripheral neuropathy, perivenous encephalomyelitis, pernicious anaemia, POEMS syndrome, polyarteritis nodosa, type I, II, and III autoimmune polyglandular syndromes, polymyalgia rheumatic, polymyositis, postmyocardial infarction syndrome, postpericardiotomy syndrome, progesterone dermatitis, primary biliary cirrhosis, primary sclerosing cholangitis, psoriasis, psoriatic arthritis, pyoderma gangrenosum, pure red cell aplasia, Raynauds phenomenon, reactive arthritis, reflex sympathetic dystrophy, Reiter's syndrome, Relapsing polychondritis, restless legs syndrome, retroperitoneal fibrosis, rheumatic fever, rheumatoid arthritis, sarcoidosis, Schmidt syndrome, scleritis, scleroderma, Sjogren's syndrome, sperm and testicular autoimmunity, Stiff person syndrome, subacute bacterial endocarditis, Susac's syndrome, sympathetic ophthalmia, systemic lupus erythematosus, Takayasu's arteritis, temporal arteritis/Giant cell arteritis, thrombocytopenic purpura, Tolosa-Hunt syndrome, transverse myelitis, type 1 diabetes, ulcerative colitis, undifferentiated connective tissue disease, uveitis, vasculitis, vesiculobullous dermatosis and vitiligo.

Examples of inflammatory or autoimmune diseases include, but are not limited to, rheumatoid arthritis, type 1 diabetes, and multiple sclerosis.

Another object of the invention is the γδ Foxp3$^+$ regulatory T cells or the γδ Foxp3$^+$ regulatory T cell population or the pharmaceutical composition as described here above for use in preventing transplant rejection, or graft versus host disease (GVHD).

In one embodiment, the γδ Foxp3$^+$ regulatory T cells are specific of at least one non-peptide phosphoantigen as described hereabove.

In another embodiment, the γδ Foxp3$^+$ regulatory T cells are specific of at least one non-peptide phosphoantigen that were present in tissue lysates.

In one embodiment, the pharmaceutical composition of the invention comprises, consists essentially of or consists of at least $10^4$, $10^5$, $10^6$, $10^7$, $10^8$, $10^9$, $10^{10}$ γδ Foxp3$^+$ regulatory T cells as active principle.

In one embodiment, the pharmaceutical composition of the invention comprises, consists essentially of or consists of about $10^4$, $5\times10^4$, $10^5$, $5\times10^5$, $10^6$, $5\times10^6$, $10^7$, $5\times10^7$, $10^8$, $5\times10^8$, $10^9$, $5\times10^9$, $10^{10}$ γδ Foxp3$^+$ regulatory T cells as active principle.

In one embodiment, the γδ Foxp3$^+$ regulatory T cells, the γδ regulatory T cell population or the pharmaceutical the invention are/is frozen.

In one embodiment, the γδ Foxp3$^+$ regulatory T cells present in the pharmaceutical composition of the invention are human γδ regulatory T cells.

In one embodiment, the γδ Foxp3$^+$ regulatory T cells present in the pharmaceutical composition of the invention are autologous γδ Foxp3$^+$ regulatory T cells.

In one embodiment, the γδ Foxp3$^+$ regulatory T cells present in the pharmaceutical composition of the invention are allogenic γδ Foxp3$^+$ regulatory T cells.

In one embodiment, the pharmaceutical composition of the invention may be administered to the subject by subcutaneous, intramuscular, intraperitoneal or intravenous injection.

In one embodiment, the pharmaceutical composition of the invention may be administered to the subject at least once, twice, 3 times, 4 times, 5 times per week.

In another embodiment, the pharmaceutical composition of the invention may be administered to the subject at least once, twice, 3 times, 4 times, 5 times per month.

In another embodiment, the pharmaceutical composition of the invention may be administered to the subject at least once, twice, 3 times, 4 times, 5 times per 3 months.

Another object of the invention is a method for treating inflammatory or autoimmune diseases in a subject in need thereof, comprising administering to the subject a therapeutically effective amount of the γδ Foxp3$^+$ regulatory T cells or the γδ Foxp3$^+$ regulatory T cell population or the pharmaceutical composition as described here above.

It has been shown in the art that T cell vaccination induces regulatory networks that specifically suppress the immunogenic T cells by activating T cells specific for a clonotype-specific determinant (anti-idiotypic response). In addition, anti-ergotypic responses directed at activation markers (corresponding to the ergotope) may also partially account for the suppression of the regulatory T cell population targeted.

Another object of the invention is an antibody recognizing the TCR (T cell receptor) of the γδ Foxp3$^+$ regulatory T cells of the invention.

In one embodiment, the antibody recognizing the TCR of the γδ Foxp3$^+$ regulatory T cells of the invention recognizes at least one of the CDR1, CDR2 and CDR3 (complementary determining region 1, 2 and 3) of the TCR.

In another embodiment, the antibody recognizing the TCR of the γδ Foxp3$^+$ regulatory T cells of the invention recognizes the CDR3 of the TCR.

Another object of the invention is a pharmaceutical composition comprising, consisting essentially of or consisting of said antibody and at least one pharmaceutically acceptable excipient.

Another object of the invention is the use of said antibody for treating cancer in a subject in need thereof.

In one embodiment, the antibodies directed against the γδ Foxp3$^+$ regulatory T cells of the invention consist of antibodies produced following immunization of a mammal, including a human, with the immunogenic composition as described here above.

In another embodiment, the antibodies may also be obtained by cloning the relevant DNA material encoding them, starting for example from B cells obtained from the said mammal, including from the said human.

In another embodiment, the antibodies may also be obtained by sequencing the amino acid sequences of the antibodies collected from the said mammal, including from the said human, and then synthesize a DNA molecule encoding the antibody or a portion thereof comprising the CDR thereof, for producing relevant recombinant antibodies directed against the γδ Foxp3$^+$ regulatory T cells of the invention.

Preparing antibodies directed against the γδ Foxp3$^+$ regulatory T cells of the invention by immunization with the immunogenic composition of the invention may be easily performed by a skilled in the art, using the common technical knowledge from the state in the art.

Alternatively, the antibodies directed against the γδ Foxp3+ regulatory T cells of the invention may be obtained after immortalization of the human B lymphocytes producing them; their cDNA can also be cloned and used further for producing them or their derivatives through recombinant DAN technology.

The term "antibody" herein is used to refer to a molecule having a useful antigen binding specificity. Those skilled in the art will readily appreciate that this term may also cover polypeptides which are fragments of or derivatives of antibodies yet which can show the same or a closely similar functionality. Such antibody fragments or derivatives are intended to be encompassed by the term antibody as used herein. By "antibody" or "antibody molecule" for the purpose of passive immunotherapy, it is intended herein not only whole immunoglobulin molecules but also fragments thereof, such as Fab, F(ab')2, Fv and other fragments thereof that retain the capacity to bind and inactivate the γδ Foxp3+ regulatory T cells. Similarly, the term antibody includes genetically engineered derivatives of antibodies such as single chain Fv molecules (scFv) and domain antibodies (dAbs).

In some embodiments, an antibody directed against the γδ Foxp3+ regulatory T cells of the invention consists of a polyclonal antibody.

In some embodiments, an antibody directed against the γδ Foxp3+ regulatory T cells of the invention consists of a monoclonal antibody.

The term "monoclonal antibody" is used herein to encompass any isolated Ab's such as conventional monoclonal antibody hybridomas, but also to encompass isolated monospecific antibodies produced by any cell, such as for example a sample of identical human immunoglobulins expressed in a mammalian cell line.

The variable heavy (VH) and variable light (VL) domains of the antibody are involved in antigen recognition, a fact first recognized by early protease digestion experiments. Further confirmation was found by "humanization" of rodent antibodies. Variable domains of rodent origin may be fused to constant domains of human origin such that the resultant antibody retains the antigenic specificity of the rodent parented antibody (Morrison et al. (1984) Proc. Natl. Acad. Sci. USA 81, 6851-6855). That antigenic specificity is conferred by variable domains and is independent of the constant domains is known from experiments involving the bacterial expression of antibody fragments, all containing one or more variable domains. These molecules include Fab-like molecules (Better et al (1988) Science 240, 1041); Fv molecules (Skerra et al (1988) Science 240, 1038); single-chain Fv (ScFv) molecules where the V.sub.H and V.sub.L partner domains are linked via a flexible oligopeptide (Bird et al (1988) Science 242, 423; Huston et al (1988) Proc. Natl. Acad. Sci. USA 85, 5879) and single domain antibodies (dabs) comprising isolated V domains (Ward et al (1989) Nature 341, 544). A general review of the techniques involved in the synthesis of antibody fragments which retain their specific binding sites is to be found in Winter & Milstein (1991, Nature 349, 293-299).

The term "ScFv molecules" encompasses molecules wherein the VH and VL partner domains are linked via a flexible oligopeptide. Engineered antibodies, such as ScFv antibodies, can be made using the techniques and approaches described in J. Huston et al, (1988) "Protein engineering of antibody binding sites: recovery of specific activity in an anti-digoxin single chain Fv analogue produced in E. coli", Proc. Natl. Acad. Sci. USA, 85, pp. 5879-5883, and in A. Pluckthun, (1991) "Antibody engineering; Advances from use of E. coli expression systems", Bio/technology 9 (6): 545-51, incorporated herein by reference.

Suitable monoclonal antibodies which are reactive as described herein may be prepared by known techniques, for example those disclosed in "Monoclonal Antibodies; A manual of techniques", H Zola (CRC Press, 1988) and in "Monoclonal Hybridoma Antibodies: Techniques and Application", S G R Hurrell (CRC Press, 1982).

A further embodiment encompasses humanized antibodies where the regions of the murine antibody that contacted the antigen, the Complementarity Determining Regions (CDRs) were transferred to a human antibody framework. Such antibodies are almost completely human and seldom cause any harmful antibody responses when administered to patients. Several chimeric or humanized antibodies have been registered as therapeutic drugs and are now widely used within various indications (Borrebaeck & Carlsson, 2001, Curr. Opin. Pharmacol. 1: 404-408).

It is preferred if the antibody is a humanized antibody. Suitably prepared non-human antibodies can be "humanized" in known ways, for example by inserting the CDR regions of mouse antibodies into the framework of human antibodies. Humanized antibodies can be made using the techniques and approaches described in Verhoeyen et al (1988) Science, 239, 1534-1536, and in Kettleborough et al, (1991) Protein Engineering, 14 (7), 773-783.

In another embodiment, antibodies also encompass completely human antibodies, which may be produced using recombinant technologies. Typically, large libraries comprising billions of different antibodies are used. In contrast to the previous technologies employing chimerization or humanization of e.g. murine antibodies this technology does not rely on immunization of animals to generate the specific antibody. Instead the recombinant libraries comprise a huge number of pre-made antibody variants wherein it is likely that the library will have at least one antibody specific for any antigen.

The frequency of administration may be determined clinically by following the decline of antibody titers in the serum of patients over time, but in any event may be at a frequency of 1 to 52 times per year, and most preferably between 1 and 12 times per year. Quantities of antibody may vary according to the severity of the disease, or half-life of the antibody in the serum, but preferably will be in the range of 1 to 10 mg/kg of patient, and preferably within the range of 1 to 5 mg/kg of patient, and most preferably 1 to 2 mg/kg of patient.

BRIEF DESCRIPTION OF THE DRAWINGS

FIG. 1: Different frequencies and phenotypic characteristics between FOXP3+ and FOXP3− CD3+ T cell populations, as defined by their variable TCR recognition in human peripheral blood (PBMCs) and in TIL isolated from breast tumor.

Frequency and (B) expression level (evaluated by MFI) of Foxp3 in CD4+ T cell culture.

FIG. 3: Phenotypic differences between the Foxp3 expressing CD3+ CD4+ γδ T cells unrestricted T cells isolated from BC biopsies and the currently described γδ T cells' subtypes. Foxp3 expressing CD3+ CD4+ γδ T cells' phenotypic identification was performed by flow cytometry using antibody against CD3 (clone SK7), CD4 (clone SK3), CD8 (clone SK1), pan γδ (clone IMMU510) and Foxp3+ (clone 259D).

Figure 4:
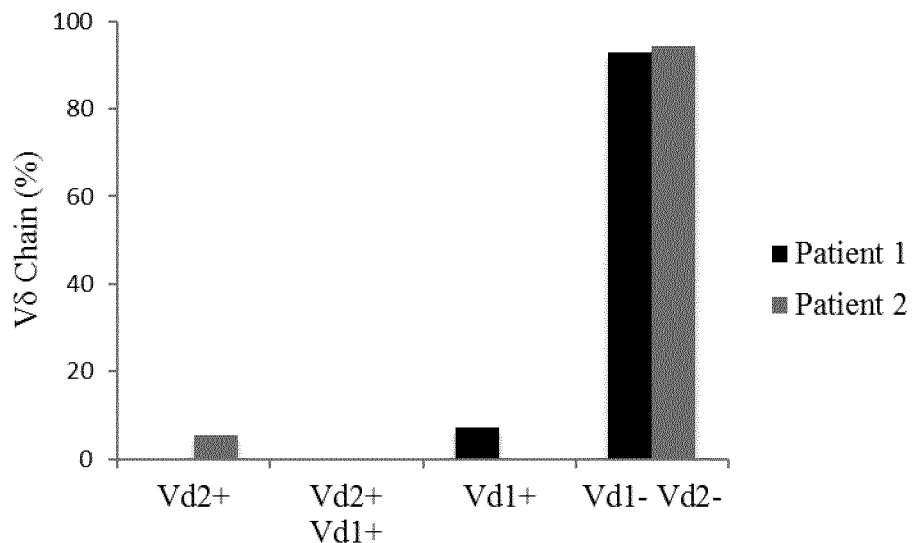

FIG. 4: TCR Vδ usage among CD3+ CD4+ γδ T cells expressing FOXP3+ isolated from BC biopsies. Identification of TCR Vγδ chains was performed by flow cytometry using antibody against CD3 (clone SK7), CD4 (clone SK3), CD8 (clone SK1), pan γδ (clone IMMU510), TCR Vδ1 (REA173), TCR Vδ2 (REA771) and Foxp3+ (clone 259D).

Figure 5:
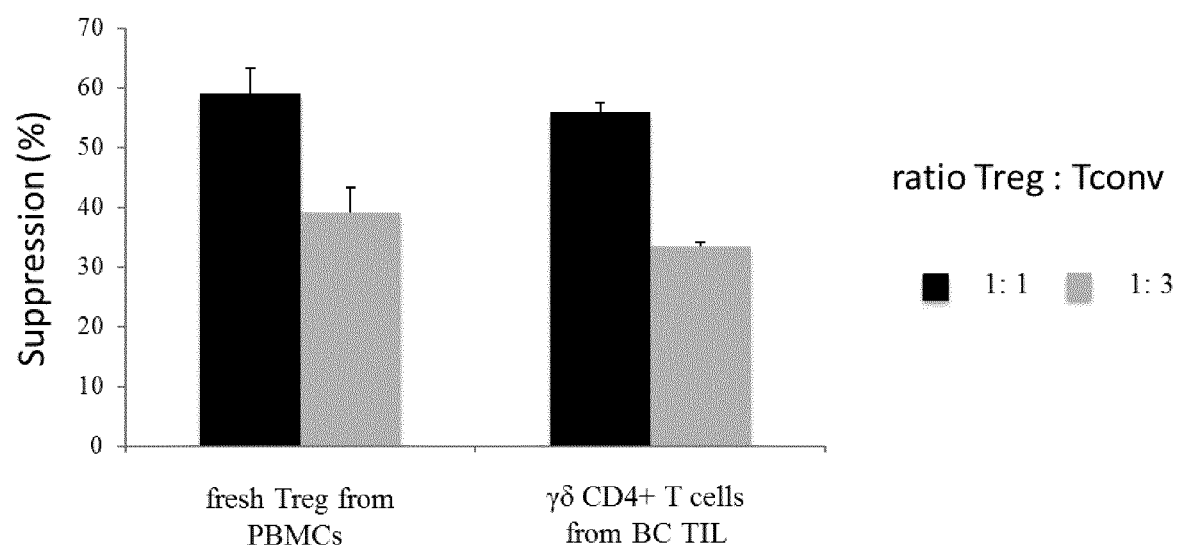

FIG. 5: Suppressive capacity of the Foxp3 expressing CD3+ CD4+ γδ T cells unrestricted T cells isolated from BC biopsies. CFSE-labeled Tconv (TconvCFSE) were cocultured with sorted CD3+ CD4+ γδ T cells at different ratios. Percent inhibition of TconvCFSE proliferation by CD4+ γδ T cells was depicted. Circulating fresh Treg from health donor were used as control.

Figure 6:
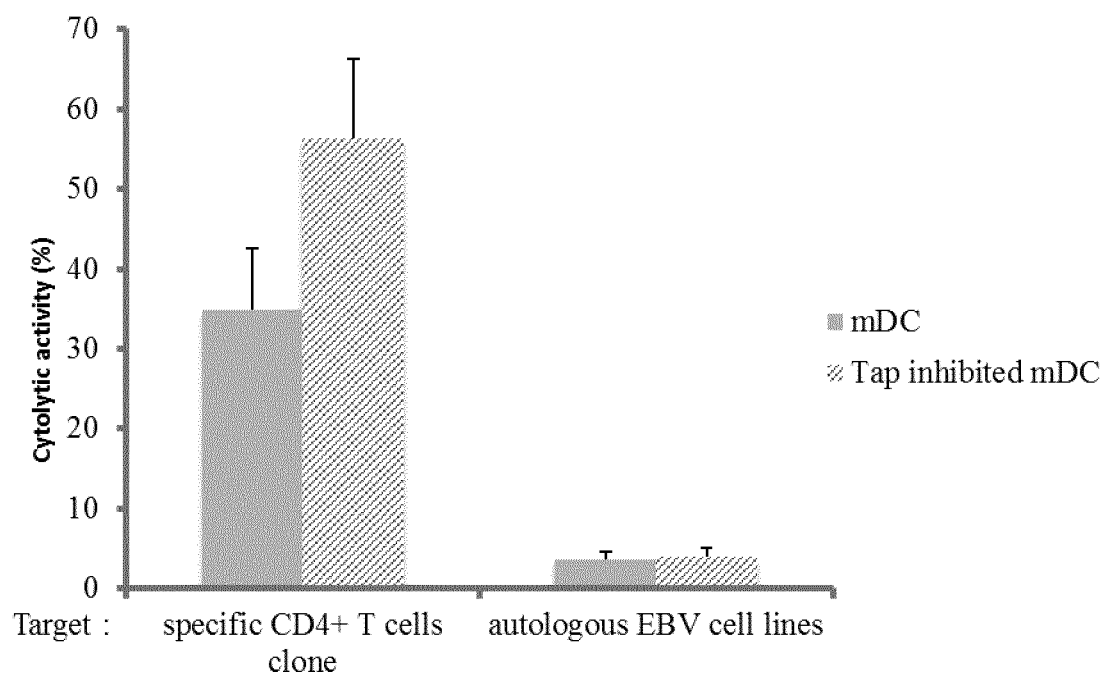

FIG. 6: Generation of autologous CD8+ T cell lines functionally committed to lyse specific pathogenic CD4+ T cells, i.e. tumor-antigen specific FOXP3 expressing CD4+ TCRγδ+ unrestricted T cells. The capacity of a CD8+ T cell clone to lyse its inducing pathogenic CD4+ T cell clone is evaluated with the classical 7-AAD/CFSE Cell-Mediated Cytotoxicity Assay as previously described. In brief, 4 days after stimulation, pathogenic CD4+ target cells or an autologous lymphoblastoid line were labeled with CFSE and placed at $3 \times 10^4$ per well in 96-well U-bottomed plates in triplicate. CD8+ Effector T cells (5:1 E:T ratio) were added, and incubation was carried out at 37° C. for 6 hours. At the end of the experiment, dead cells were labeled with 7-AAD to detect lysed cells. Cytolytic activity against target cells was analyzed based on regions showing double-positive staining CFSE and 7-AAD, using a FACSCalibur instrument. CD8+ T cell clone cytolytic activity (%) was calculated as cells positive for both CFSE and 7-AAD/total CFSE positive cells, after subtracting the spontaneous lysis (%) in negative control. The percentage of cytolytic activity was then calculated using the following equation: Cytolytic activity (%) [dead target cells (%)–spontaneous death (%)]×100/[100–spontaneous death (%)].

FIG. 7: Analysis of Foxp3+ expression in lymphocytes present in the TILs extracted from luminal A and B breast subtypes. Tumor tissue from patient with luminal-A and luminal B was minced with scalpels and enzymatically digested by overnight incubation in collagenase Type IV. Expression of FOXP3 marker in lymphocytes present in the isolated TIL was determined by flow cytometric analysis.

Figure 8:
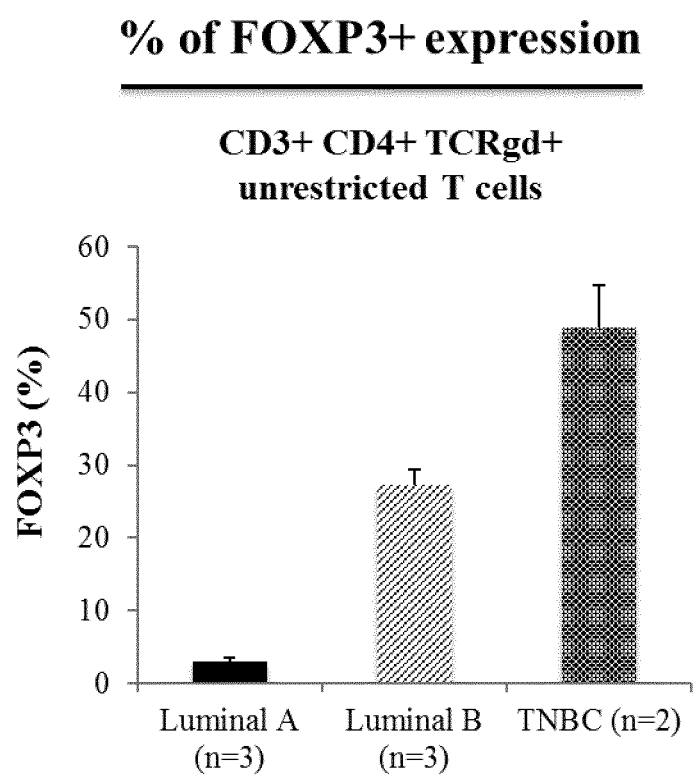

FIG. 8: Analysis of Foxp3+ expression in lymphocytes present in the TILs extracted from 3 different breast cancers' subgroups: tumor tissue from patient with luminal A (n=3), luminal B (n=3) and patients with triple-negative breast cancer (TNBC) (n=2) was minced with scalpels and enzymatically digested by overnight incubation in collagenase Type IV. Expression of FOXP3 marker in lymphocytes present in the isolated TIL was determined by flow cytometric analysis. Representation of the percentage of FOXP3 expression in the CD3+CD4+TCRγδ+ unrestricted T cells.

Figure 9:
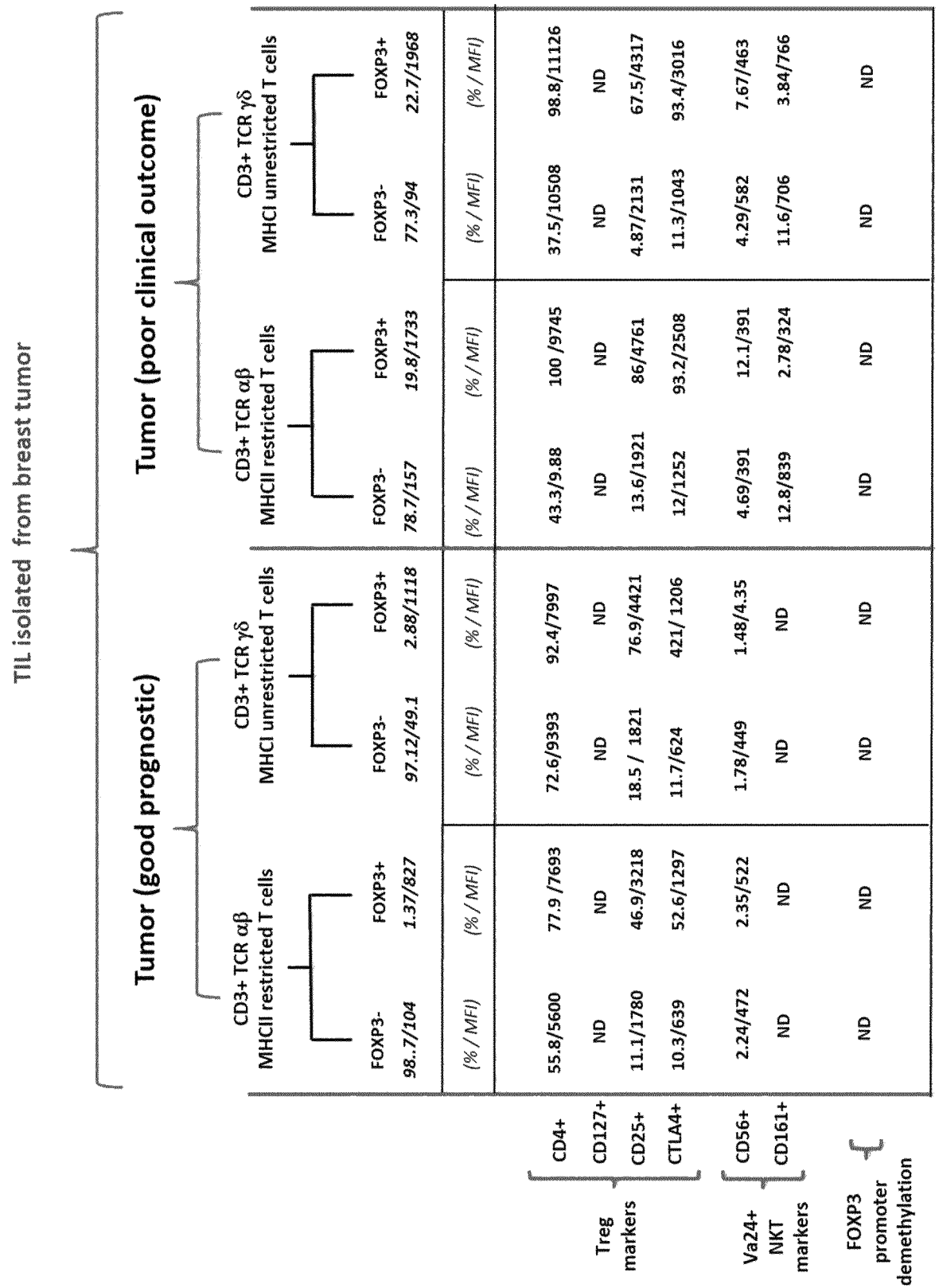

FIG. 9: Multiparametric flow cytometry analysis of lymphocytes present in the TILs from luminal A and B breast subtypes. Lymphocytes present in the TIL were stained at the cell surface using Abs directed against CD3, CD4, CD25, CD56, CD161. After fixation and permeabilization Foxp3 and CTLA4 were stained intracellularly.

Figure 10:
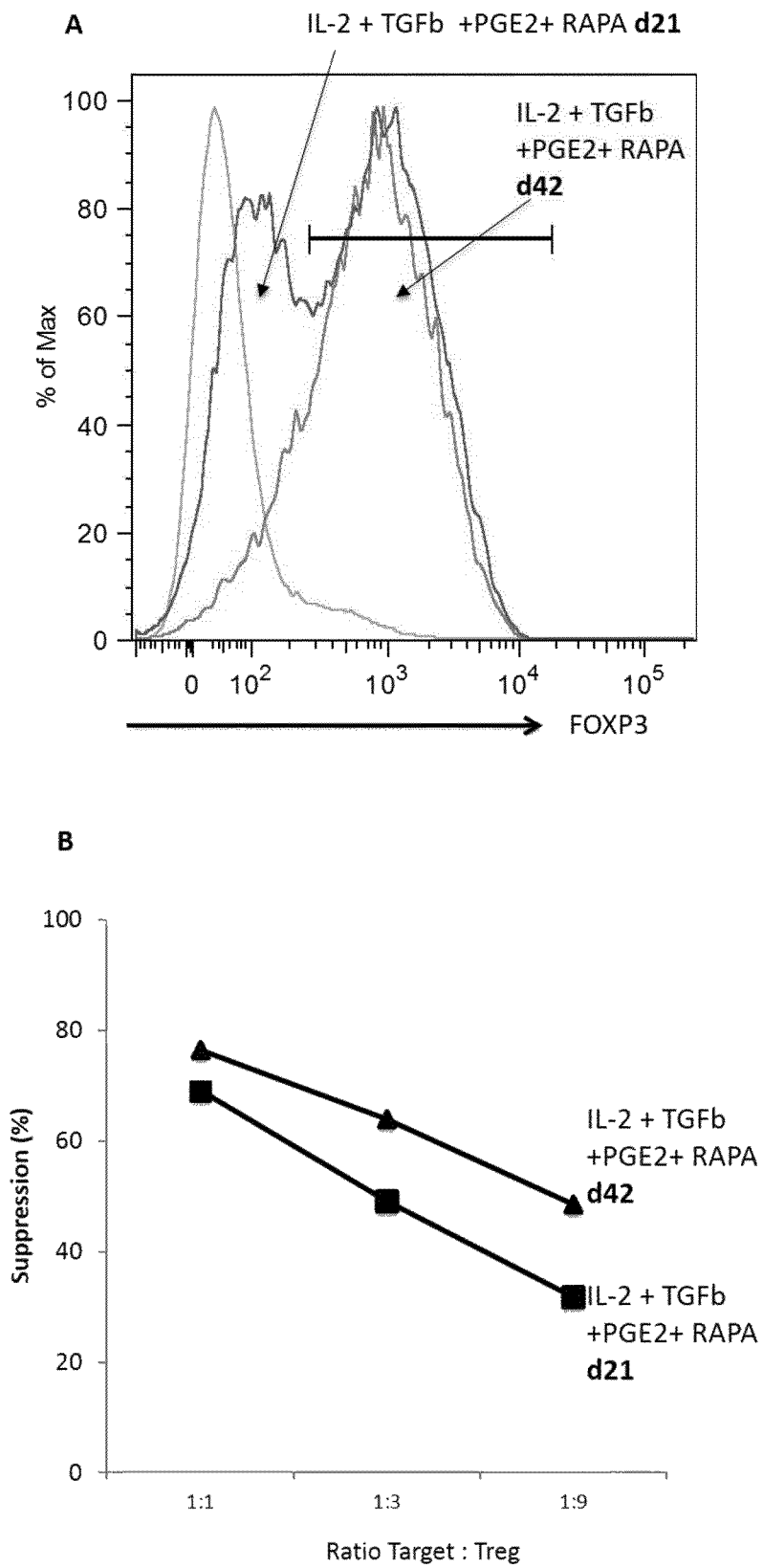

FIG. 10: Phenotype and functional suppressive capacity of ex vivo generated Ag specific CD3+ TCRγδ+ T cells from stimulated naive CD3+ TCRγδ+ T cells. Naive CD3+ TCRγδ+ T cells were stimulated with zoledronic acid-treated-autologous tDCs, in presence of the nTreg polarizing medium and IL-2 (100 IU/ml) and IL-15 (10 ng/ml). (A) Overlay histogram displaying Foxp3 expression profiles and (B) suppressive capacity of Ag specific CD3+ TCRγδ+ T cells expanded for 21 or 42 days.

EXAMPLES

The present invention is further illustrated by the following examples.

Materials and Methods

Human Blood Sample. Blood samples from healthy individuals originated from Etablissement Français du Sang (EFS, Paris). Blood cells are collected using standard procedures.

Human tumor sample. Tumor tissue sample originated from patient with Luminal A and Luminal B Breast cancer (Institut Jean Godinot, Reims).

Cell Purification and Culture.

Peripheral blood mononuclear cells (PBMCs) are isolated by density gradient centrifugation on Ficoll-Hypaque (Pharmacia). PBMCs are used either as fresh cells or stored frozen in liquid nitrogen. T-cell subsets and T cell-depleted accessory cells (ΔCD3 cells) are isolated from either fresh or frozen PBMCs. T cell-depleted accessory cells (ΔCD3 cells) are isolated by negative selection from PBMCs by incubation with anti-CD3-coated Dynabeads (Dynal Biotech) and are irradiated at 3000 rad (referred to as ΔCD3-feeder).

CD4+ T cells are negatively selected with a CD4+ T-cell isolation kit (Miltenyi Biotec, yielding CD4+ T-cell populations at a purity of 96-99%. Sub-sequently, selected CD4+ T cells are labeled with anti-CD4 (13B8.2)-FITC (Beckman Coulter), anti-CD25(4E3)-APC (Miltenyi Biotec), and anti-CD127(R34.34)-PE (Beckman Coulter) before being sorted into CD4+CD127$^{-/lo}$CD25$^{high}$(pTregs) and CD4+CD127+CD25$^{neg/dim}$ [conventional helper CD4 T cells (Tconv)] subpopulations using a FACSAria III Cell Sorter (Becton Dickinson).

CD14+ monocytes are isolated from PBMCs by positive selection using a MACS system.

CD3+ CD4+ CD127+ CD45RA+ CD25− TCRαβ+ MHCII restricted (naive conventional CD4+ T cells) are isolated from PBMCs after magnetic enrichment (MACS system: CD4 microbeads) and FACs sorting. Before the sorting step, enriched CD3+ CD4+ T cells are stained with anti-CD4 (13B8.2)-FITC (Beckman Coulter), anti-CD25(4E3)-APC (Miltenyi Biotec), and anti-CD127(R34.34)-PE (Beckman Coulter), anti-TCR αβ-BV421 (IP26) (Biolegend).

CD3+ CD45RA+ invTCR Vα24+ CD1-restricted T cells are isolated from PBMCs after magnetic enrichment (MACS system: anti-iNKT microbeads and FACS sorting. Before the sorting step, enriched CD3+ invTCR Vα24+T cells are stained with anti-CD3 (UCHT-1) V450 anti-invariant TCR Vα24-JαQ (6B11)-PE (inv TCR Vα24-JαQ (Becton Dickinson) and anti-CD45RA (T6D11)-FITC (Miltenyi Biotec).

CD3+ CD45RA+ CD27+ TCRγδ+ unrestricted T cells are isolated from PBMCs after magnetic enrichment (MACS system: TCRγδ+ T cell isolation kit) and FACS sorting. Before the sorting step, enriched CD3+ TCRγδ+ T cells are stained with anti-CD3 (UCHT-1) V450, anti-TCR panγδ+

PE (IMMU510) (Beckman Coulter), anti-CD27-APC efluor 780 (O323) (ebioscience) and anti-CD45RA (T6D11)-FITC (Miltenyi Biotec).

T cell subsets are cultured either in IMDM supplemented with 5% SVF, 100 IU/ml penicillin/streptomycin, 1 mM sodium pyruvate, 1 mM nonessential amino acids, glutamax and 10 mM HEPES (IMDM-5 media) in hypoxia 2%.

Breast cancer cell line and culture. The human breast cancer cell line MCF-7 was obtained from the American Type Culture Collection (USA). Cells are maintained in Dulbecco's modified Eagle's medium (DMEM; Invitrogen, USA) supplemented with 10% fetal bovine serum (FBS). MCF-7 cells are treated with 5 μg/ml Doxorubicin for 24 h or by γ irradiation (20 Gy). Extent of apoptosis is monitored by flow cytometric analysis (FACS). Cells are extensively washed prior to feeding DCs.

TIL isolation. Tumor tissue was minced with scalpels and enzymatically digested by overnight incubation in collagenase Type IV (2 mg/mL, Roche Diagnostic GmbH) in DMEM High Glucose medium supplemented with 2 mM glutamine (Gibco), 50 mg/mL gentamycin and 0.25% Human Serum Albumin, at 37° C. on a rotary shaker.

Ex Vivo Generation of Polyclonal Functionally Committed FOXP3 Expressing Regulatory T Cells.

Ex vivo generation of polyclonal functionally committed FOXP3 expressing CD3$^+$ TCRαβ$^+$ MHCII restricted T cells: On day 0, T cells are seeded at 2.5×10$^5$/well in 48-well plates and stimulated with plate-bound anti-CD3 mAb (4 μg/ml) in the presence of ΔCD3-feeder (1 M). Cells are cultured in IMDM-5 media (IMDM supplemented with 5% SVF, 100 IU/ml penicillin/streptomycin, 1 mM sodium pyruvate, 1 mM nonessential amino acids, glutamax and 10 mM HEPES) with PGE2 1 μM, TGFβ 5 ng/ml, Rapa 10 nM. On day 2, IL-2 (100 IU/ml) are added to the culture. Every three days, half of the supernatant volume is discarded and replaced with fresh IMDM-5 with IL-2 (100 UI/ml). On day 11, these CD4$^+$ T-cell lines were further expanded by restimulation with plate-bound anti-CD3 Abs (4 μg/ml). The restimulations were performed in the presence of ΔCD3-feeder, PGE2 1 μM, TGFβ 5 ng/ml, Rapa 10 nM and IL-2 (100 UI/ml). Then every three days, half of the supernatant volume is discarded and replaced with fresh IMDM-5 with IL-2 (100 UI/ml). On day 20, the phenotype of the expanded CD4$^+$ T cells was assessed by flow cytometry. 75% of the stimulated naive conventional T cells that became CD45RO$^+$ express FOXP3$^+$.

Ex vivo generation of polyclonal functionally committed FOXP3 expressing invariant T cells: On day 0, T cells are seeded at 1×10$^3$/well in 96-well plates and stimulated with plate-bound anti-inv TCR Vα24-JαQ (6B11) mAb (2 μg/ml) in the presence of ΔCD3-feeder (2.5×10$^5$). Cells are cultured in IMDM-5 media with PGE2 1 μM, TGFβ 5 ng/ml, Rapa 10 nM, IL-2 (100 UI/ml) and IL-15 (10 ng/ml). Every three days, IL-2 (100 UI/ml) and IL-15 (10 ng/ml) are added to the culture. On day 12, T cells are further expanded by restimulation with plate-bound anti-anti-inv TCR Vα24-JαQ (6B11) mAb (2 μg/ml) in the presence of ΔCD3-feeder, PGE2 1 μM, TGFβ 5 ng/ml, Rapa 10 nM IL-2 (100 UI/ml) and IL-15 (10 ng/ml). Then every three days, half of the supernatant volume is discarded and replaced with fresh IMDM-5 with IL-2 (100 UI/ml) and IL-15 (10 ng/ml). On day 21, cells are analyzed by flow cytometry. 70% of the stimulated CD3+ invTCR Vα24$^+$ RA$^+$ T cells that became CD45RO$^+$ express Foxp3$^+$.

Ex vivo generation of polyclonal functionally committed FOXP3 expressing TCRγδ$^+$ T cells: On day 0, T cells are seeded at 1×10$^3$/well in 96-well plates and stimulated with plate-bound anti-TCRγδ mAb (2 μg/ml) in the presence of ΔCD3-feeder (2.5×10$^5$). Cells are cultured in IMDM-5 media (IMDM supplemented with 5% SVF, 100 IU/ml penicillin/streptomycin, 1 mM sodium pyruvate, 1 mM nonessential amino acids, glutamax and 10 mM HEPES) with PGE2 1 μM, TGFβ 5 ng/ml, Rapa 10 nM, IL-2 (100 UI/ml) and IL-15 (10 ng/ml). Every three days, half of the supernatant volume is discarded and replaced with fresh IMDM-5 with IL-2 (100 UI/ml) and IL-15 (10 ng/ml). On day 11, T cells were further expanded by restimulation with plate-bound anti-pan TCR γδ Abs (2 μg/ml). The restimulations were performed in the presence of ΔCD3-feeder, PGE2 1 μM, TGFβ 5 ng/ml, Rapa 10 nM and IL-2 (100 UI/ml) and IL-15 (10 ng/ml). Then every three days, half of the supernatant volume is discarded and replaced with fresh IMDM-5 with IL-2 (100 UI/ml) and IL-15 (10 ng/ml). On day 21, cells are analyzed by flow cytometry. 65% of the stimulated CD3$^+$ CD45RA$^+$ CD27$^+$ TCRγδ$^+$ T cells that became CD45RO$^+$ express Foxp3$^+$.

Ex Vivo Generation of Antigen Specific Functionally Committed FOXP3 Expressing T Cells.

Ex Vivo Generation of Antigen (Ovalbumin) Specific Functionally Committed FOXP3 Expressing CD3$^+$ TCRαβ$^+$ MHCII Restricted T Cells:

a) In vitro generation of ovalbumin-loaded tolerogenic DC from CD14$^+$ monocytes (termed tolerogenic monocyte-derived DC (Tol-Mo-DC): monocytes are cultured in 48-well flat-bottom plates containing 0.5 ml of AIMV per well supplemented with 100 ng/ml recombinant human granulocyte-macrophage colony-stimulating factor (GM-CSF) and 10 ng/ml human recombinant IL-4 for the generation of immature DC. At day 3, 500 μl of the medium containing cytokines was added. On day 6, Tol-Mo-DC are 1) removed from the wells, washed twice with IMDM-5 (IMDM supplemented with 5% SVF, 100 IU/ml penicillin/streptomycin, 1 mM sodium pyruvate, 1 mM nonessential amino acids, glutamax and 10 mM HEPES, 2) added to wells of a 48-well plate at a concentration of 3×10$^5$/ml in IMDM-5 and 3) pulsed in IMDM-5 with specific Ag (OVA).

b) Ex vivo generation and expansion of specific functionally committed FOXP3 expressing CD3$^+$ TCRαβ$^+$ MHCII restricted T cells: On day 0, ovalbumin pulsed tDC are 1) washed twice with IMDM-5 and 2) added to wells of a 48-well plate at a concentration of 3×10$^5$/ml in IMDM-5 in the presence of 2×10$^5$ irradiated autologous feeders, PGE2 1 μM, and Rapa 10 nM. Purified naive conventional CD4$^+$ T cells (isolated from the previously frozen PBMC by FACS) are added to the pulsed tDC. On day 1, IL-2 (100 IU/ml) and TGFβ (5 ng/ml) are added to the coculture. Every three days, half of the supernatant volume is discarded and replaced with fresh IMDM-5 with IL-2 (100 UI/ml (T cell cloning medium). On day 12, these T-cells are further expanded by restimulation with ova-pulsed tDC in the presence of ΔCD3-feeder, PGE2 1 μM, TGFβ 5 ng/ml, Rapa 10 nM, IL-2 (100 UI/ml). Once T cells begin to expand, they can be split every 2 to 3 days with T cell cloning medium and irradiated feeder. On day 21, cells are analyzed by flow cytometry. 85% of the stimulated naive conventional CD4$^+$ T cells that became CD45RO$^+$ express Foxp3$^+$. To confirm that the Ova-specific memory CD3$^+$ TCRαβ$^+$ MHCII restricted T cells are committed to exclusively exert regulatory activity, whatever culture condition of stimulation, after 21 days of expansion in nTreg polarizing medium, the ova-specific-pTreg are further cultured for 3 weeks either in nTreg polarizing medium (comprising the combination of IL-2, TGFβ, PGE2 and rapamycin) or TH-17 polarizing medium (IMDM medium containing IL-2 IL-1 IL-6, IL-21 IL-23 cytokines). The 21-day-expanded-Foxp3 expressing CD3$^+$ CD4$^+$ TCRαβ$^+$ MHCII restricted T cells are stimulated with plate-bound anti-CD3 mAb (4 μg/ml) in the presence of ΔCD3-feeder (1 M) in 48-well plates and every three days, half of the supernatant volume is discarded and replaced with fresh T cell cloning medium or TH-17 polarizing medium for 21 days.

Ex Vivo Generation of Specific Tumor Phospho-Antigen Functionally Committed FOXP3 Expressing CD3$^+$ TCRγβ$^+$ Unrestricted T Cells:

In vitro generation of tumor-loaded tolerogenic DC from CD14$^+$ monocytes (termed tolerogenic monocyte-derived DC (tDC)): monocytes are cultured in 48-well flat-bottom plates containing 0.5 ml of AIMV per well supplemented with 100 ng/ml recombinant human granulocyte-macrophage colony-stimulating factor (GM-CSF) and 10 ng/ml human recombinant IL-4. At day 3, 500 μl of the medium containing cytokines are added. At day 5, a portion of tDCs are co-cultured with apoptotic MCF-7 cells at a DC/tumor cell ratio of 1:2 for 24 h in AIMV with GM-CSF (100 ng/mL), IL-4 (10 ng/mL). Another portion of tDC are freezed at $2 \times 10^6$/per vial—in 90% FBS—10% DMSO.

Ex Vivo Generation and Expansion of Tumor-Phospho-Antigen Specific Functionally Committed Foxp3 Expressing CD3$^+$ TCRγβ$^+$ Unrestricted T Cells:

On day 0, tumor-antigen pulsed tDC are 1) washed twice with IMDM-5 and 2) added to wells of a 48-well plate at a concentration of $3 \times 10^5$/ml in IMDM-5 in the presence of $2 \times 10^5$ irradiated autologous feeders, PGE2 1 μM, and Rapa 10 nM. Purified CD3$^+$ CD45RA$^+$ TCRγδ$^+$ unrestricted T cells (isolated from the previously frozen PBMC by FACS) are added to the pulsed tDC. On day 1, IL-2 (100 IU/ml) and TGFβ (5 ng/ml) are added to the coculture. Every three days, half of the supernatant volume is discarded and replaced with fresh IMDM-5 with IL-2 (100 UI/ml) (T cell cloning medium). On day 12, these T-cells are further expanded by restimulation with tumor Ag-pulsed tDC in the presence of ΔCD3-feeder, PGE2 1 μM, TGFβ 5 ng/ml, Rapa 10 nM and IL-2 (100 UI/ml). Once T cells begin to expand, they can be split every 2 to 3 days with T cell cloning medium and irradiated feeder. On day 21, cells are analyzed by flow cytometry. 75% of the stimulated naive CD3$^+$ CD45RA$^+$ TCRγδ$^+$ T cells that became CD45RO$^+$ express Foxp3$^+$.

Ex Vivo Generation of Tumor-Antigen Specific Functionally Committed FOXP3 Expressing CD3$^+$ invTCR Vα24$^+$ CD1d-Restricted T Cells:

a) In vitro generation of tumor-loaded Tolerogenic DC from CD14$^+$ monocytes (termed tolerogenic monocyte-derived DC (tDC): monocytes are cultured in 48-well flat-bottom plates containing 0.5 ml of AIMV per well supplemented with 100 ng/ml recombinant human granulocyte-macrophage colony-stimulating factor (GM-CSF) and 10 ng/ml human recombinant IL-4 and AM580 (100 nM) for the generation of immature DC expressing CD1d. At day 3, 500 μl of the medium containing cytokines are added. At day 5, a portion of tDCs are co-cultured with apoptotic MCF-7 cells at a DC/tumor cell ratio of 1:2 for 24 h in AIMV with GM-CSF (100 ng/mL), IL-4 (10 ng/mL). Another portion of tDC are freezed at $2 \times 10^6$/per vial vial—in 90% FBS –10% DMSO.

b) Ex vivo generation and expansion of tumor-antigen specific functionally committed Foxp3 expressing CD3$^+$ invTCR Vα24$^+$ CD1d-restricted T cells: On day 0, tumor-antigen pulsed tDC are 1) washed twice with IMDM-5 and 2) added to wells of a 48-well plate at a concentration of $3 \times 10^5$/ml in IMDM-5 in the presence of $2 \times 10^5$ irradiated autologous feeders, PGE2 1 μM, and Rapa 10 nM. Purified CD3$^+$ CD45RA$^+$ invTCR Vα24$^+$ CD1-restricted T cells (isolated from the previously frozen PBMC by FACS) are added to the pulsed tDC. On day 1, IL-2 (100 IU/ml), IL-15 (10 ng/ml) and TGFβ (5 ng/ml) are added to the coculture. Every three days, half of the supernatant volume is discarded and replaced with fresh IMDM-5 with IL-2 (100 UI/ml) and IL-15 (10 ng/ml) (T cell cloning medium). On day 12, these T-cells are further expanded by restimulation with tumor Ag-pulsed tDC in the presence of ΔCD3-feeder, PGE2 1 μM, TGFβ 5 ng/ml, Rapa 10 nM, IL-2 (100 UI/ml) and IL-15 (10 ng/ml). Once T cells begin to expand, they can be split every 2 to 3 days with T cell cloning medium and irradiated feeder. On day 21, cells are analyzed by flow cytometry. 75% of the stimulated CD3$^+$ CD45RA$^+$ invTCR Vα24$^+$ cells that became CD45RO$^+$ express Foxp3$^+$.

Ex Vivo Generation of Phospho-Antigen Specific Functionally Committed FOXP3 Expressing CD3$^+$ TCRγδ$^+$ Unrestricted T Cells:

a) In vitro generation of Tolerogenic DC from CD14$^+$ monocytes (termed tolerogenic monocyte-derived DC (Tol-Mo-DC): monocytes are cultured in 48-well flat-bottom plates containing 0.5 ml of AIMV per well supplemented with 100 ng/ml recombinant human granulocyte-macrophage colony-stimulating factor (GM-CSF) and 10 ng/ml human recombinant IL-4 for the generation of immature DC. At day 3, 500 μl of the medium containing cytokines was added. On day 6, generated Tol-Mo-DC are removed from the wells, washed twice with IMDM-5 (IMDM supplemented with 5% SVF, 100 IU/ml penicillin/streptomycin, 1 mM sodium pyruvate, 1 mM nonessential amino acids, glutamax and 10 mM HEPES, freezed or used for the generation and expansion of phospho-antigen specific functionally committed FOXP3 expressing CD3$^+$ TCRγδ$^+$ unrestricted T cells.

b) Ex vivo generation and expansion of phospho-antigen specific functionally committed FOXP3 expressing CD3$^+$ TCRγδ$^+$ unrestricted T cells: On day 0, tDC are added to wells of a 48-well plate at a concentration of $3 \times 10^5$/ml in IMDM-5 in the presence of $2 \times 10^5$ irradiated autologous feeders, PGE2 1 μM, and Rapa 10 nM and zoledronic acid (100 nM). Purified CD3$^+$ CD45RA$^+$ TCRγδ$^+$ unrestricted T cells (isolated from the previously frozen PBMC by FACS) are added to the pulsed tDC. On day 1, IL-2 (100 IU/ml), IL-15 (10 ng/ml) and TGFβ (5 ng/ml) are added to the coculture. Every three days, half of the supernatant volume is discarded and replaced with fresh IMDM-5 with IL-2 (100 UI/ml) and IL-15 (10 ng/ml) (T cell cloning medium). On day 12, these T-cells are further expanded by restimulation with tDC in the presence of ΔCD3-feeder, PGE2 1 μM, TGFβ 5 ng/ml, Rapa 10 nM, IL-2 (100 UI/ml), IL-15 (10 ng/ml) and zoledronic acid (100 nM). Once T cells begin to expand, they can be split every 2 to 3 days with T cell cloning medium and irradiated feeder. On day 21, cells are analyzed by flow cytometry. 75% of the stimulated CD3$^+$ CD45RA$^+$ TCRγδ$^+$ T cells that became CD45RO$^+$ express Foxp3$^+$.

In vitro generation of stimulator cells for MLR assay: monocytes are cultured in 48-well flat-bottom plates containing 0.5 ml of RPMI-5 per well supplemented with 20 ng/ml recombinant human granulocyte-macrophage colony-stimulating factor (GM-CSF) and 20 ng/ml human recombinant IL-4 for the generation of immature DC (iDC). At day 3, 500 μl of the medium containing cytokines are added. At day 5, a portion of iDC are co-cultured with apoptotic MCF-7 cells at a DC/tumor cell ratio of 1:2 for 24 h in RPMI 1640 supplemented with GM-CSF (20 ng/mL), IL-4 (20 ng/mL) and 5% FBS. Another portion of iDC are freezed at 2×10$^6$/per vial—in 90% FBS—10% DMSO. When indicated, pulsed DCs are matured with tumor necrosis factor α (TNF-α; 20 ng/mL final) and PGE2 (1 μM) for 2 days (mDC). In some experiments, TNF and PGE2 (at the same concentrations), or lipopolysaccharide (LPS; 10-1000 ng/mL; Sigma) are added directly to MLRs. Antigen-loaded DC stimulators are irradiated at 30 Gy.

In vitro generation of TAP-inhibited stimulator cells for MLR assay: matured DC, obtained as described above, are electroporated with 20 μg of RNA synthesized from the pGem4Z vector containing the UL49.5 gene from BHV-1. (ref: Lampen M H, Verweij M C, Querido B, van der Burg S H, Wiertz E J, van Hall T. CD8$^+$ T cell responses against TAP-inhibited cells are readily detected in the human population. (J Immunol. 2010 Dec. 1; 185(11):6508-17.)

Apoptotic T cells-DC cocultures: immature DCs were cultured alone or with apoptotic cells (3 apoptotic cells: 1 iDC) for 16 h. DCs were then purified by immunomagnetic depletion of apoptotic T cells using anti-CD3-coated microbeads (Miltenyi Biotec), electroporated or not with 20 μg of synthesized RNA and incubated in RPMI-5 supplemented with 20 ng/ml GM-CSF, 20 ng/ml human recombinant IL-4 and the maturation cocktail (TNF-α 20 ng/ml and PGE2 1 μM) for 24 hours.

Flow Cytometry Analysis mAb labeling. The following conjugated mAbs are used.
a) for CD3$^+$ T cells: anti-CD4(SK3)-PerCP-eFluor 710, anti-TCR αβ (IP26)-APC (ebioscience), anti-CD25 (B1.49.9)-PeCy55, anti-CD127 (R34.34)-APC-AF700 (Beckman Coulter), anti-CD3 (UCHT1)-BB515 anti-invariant TCR Vα24-JαQ (6B11)-PE, anti-Foxp3 (259D/C7)-PE-CF594 and anti-CD152 (BNI3)-BV421, anti-CD161 (DX12) BV605 and anti-CD56 (NCAM 16.2) BU395 (Becton Dickinson), anti-TCR αβ-BV421 (IP26) (Biolegend), anti-TCR pan γδ$^+$ PE (IMMU510) (Beckman Coulter) and anti-CD27-APC efluor 780 (O323) (ebioscience). Cells are stained for surface markers (at 4° C. in the dark for 30 min) using mixtures of Ab diluted in PBS containing BSA/NaN$_3$ (0.5% BSA, 0.01% NaN$_3$) (FACS buffer). Foxp3 and CTLA-4 intracellular stainings are performed with FOXP3 staining kit obtained from ebioscience according to the manufacturer's instructions. Appropriate isotype control Abs are used for each staining combination. Samples are acquired on a BD LSR FORTESSA flow cytometer using BD FACSDIVA 8.0.1 software (Becton Dickinson). Results are expressed in percentage (%) or in mean fluorescence intensity (MFI).

b) for the induced specific Treg: presence of IL-1R1 on induced Treg was evaluated with the monoclonal anti-Foxp3 (259D/C7)-PE-CF594 Ab and the polyclonal anti-IL1R1-PE (R&D system, FAB269P).

CFSE staining. Tconv are stained with 1 μM carboxy-fluorescein succinimidyl ester (CFSE) (CellTrace cell proliferation kit; Molecular Probes/Invitrogen) in PBS for 8 min at 37° C. at a concentration of 1×10$^7$ cells/mL. The labeling is stopped by washing the cell twice with RPMI 1640 culture medium containing 10% FBS. Cells are then resuspended at the desired concentration and subsequently used for proliferation assays.

7-AAD (7-amino-actinomycin D) staining. Apoptosis of stimulated CFSE-labeled or unlabeled nTregs and Tconv was determined using the 7-AAD assay. Briefly, cultured cells are stained with 20 μg/mL nuclear dye 7-AAD (Sigma-Aldrich) for 30 min at 4° C. FSC/7-AAD dot plots distinguish living (FSC$^{high}$/7-AAD$^-$) from apoptotic (FSC$^{high}$/7-AAD$^+$) cells and apoptotic bodies (FSC$^{low}$/7-AAD$^+$) and debris ((FSC$^{low}$/7-AAD$^-$). Living cells are identified as CD3+ 7-AAD$^-$ FSC$^+$ cells.

Phenotypic characteristics of the Foxp3 expressing CD3+ CD4+ γδ T cells unrestricted T cells isolated from BC biopsies: TCR γδ T cells' subset identification was performed by flow cytometry. The panel included antibody against CD3 (clone SK7), CD4 (clone SK3), CD8 (clone SK1), pan γδ (clone IMMU510), TCR Vδ1 (REA173), TCR Vδ2 (REA771) and Foxp3+ (clone 259D).

Functional Assays.

T-cell proliferation. T-cell proliferation is assessed CFSE dilution assay in RPMI supplemented with 5% FBS, 100 IU/ml penicillin/streptomycin, 1 mM sodium pyruvate, 1 mM nonessential amino acids, glutamax and 10 mM HEPES (RPMI-5 media) in normoxia. At coculture completion, stimulated CFSE-labeled Tconv are harvested, costained with anti-CD3 mAb and 7-AAD, and the percentage of living proliferating cells (defined as CFSE low fraction) in gated CD3$^+$ 7-AAD$^-$ cells is determined by flow cytometry.

T cell apoptosis induction: tumor-antigen specific functionally committed FOXP3 expressing CD3$^+$ TCRγδ$^+$ unrestricted T cells are generated ex vivo as described above. Then tumor-antigen specific stimulated-T cells were irradiated (240 mJ/cm$^2$) at 254 nm (UV-C) and cultured for 6 hours before coculture with immature DCs. Apoptosis was confirmed by 7-AAD staining. On average, 75% of cells are 7-AAD$^+$.

Standard polyclonal cell-cell contact Treg suppression assay: CFSE-labeled Tconv (4×10$^4$ per well), used as responder cells, are cultured with ΔCD3-feeder (4×10$^4$ per well) in the presence or absence of defined amounts of Foxp3 T cells (blood Treg or ex vivo generated T cells) for 4 to 5 d. Cultures are performed in round-bottom plates coated with 0.2 μg/mL anti-CD3 mAb in 200 μL of complete RPMI medium. Results are expressed as the percentage of proliferating CFSE low T cells or as a percentage of suppression calculated as follows: (100×[(percentage of Tconv CFSE low cells−percentage of Tconv CFSE low in coculture with nTregs)/percentage of Tconv CSFE low cells].

Autologous MLR suppression assay: CFSE-labeled Tconv CD4$^+$CD25$^-$ T cells (5×10$^4$) are stimulated either with 1×10$^4$ pulsed iDC in RPMI-5 media or with 5×10$^3$ pulsed—mDC in IMDM-5 media supplemented with IL-2 (20 IU/ml) IL-1b (10 ng/ml), IL-6 (30 ng/ml), IL-21 (50 ng/ml) and IL-23 (30 ng/ml) in the presence or absence of defined amounts of Foxp3 T cells (blood Treg or ex vivo generated T cells) for 5 to 6 d. When indicated, culture is performed in IMDM-5 media supplemented with IL-2 (20 IU/ml) IL-1β (10 ng/ml), IL-6 (30 ng/ml), IL-21 (50 ng/ml) and IL-23 (30 ng/ml). Results are expressed as the percentage of proliferating CFSE low T cells or as a percentage of suppression calculated as follows: (100×[(percentage of Tconv CFSE low cells−percentage of Tconv CFSE low in coculture with nTregs)/percentage of Tconv CSFE low cells.

Classical 7-AAD/CFSE Cell-Mediated Cytotoxicity Assay: target cells were labeled with CFSE as described above and placed at 3×10$^4$ per well in 96-well U-bottomed plates in triplicate. CD8$^+$ effector T cells (5:1 E:T ratio) were added, and incubation was carried out at 37° C. for 6 hours. At the end of the experiment, dead cells were labeled with 7-AAD to detect lysed cells. Cytolytic activity against target cells was analyzed based on regions showing double-positive staining CFSE and 7-AAD, using a FACSCalibur instrument. CD8$^+$ T cell clone cytolytic activity (%) was calculated as cells positive for both CFSE and 7-AAD/total CFSE positive cells, after subtracting the spontaneous lysis (%) in negative control. The percentage of cytolytic activity was then calculated using the following equation: Cytolytic activity (%) [dead target cells (%)−spontaneous death (%)]× 100/[100−spontaneous death (%)].

Measurement of DNA methylation: Classically, a stable Treg genetic signature consisted of highly demethylated CpG islands within the conserved non-coding sequence 2 (CNS2) of the Treg specific demethylation region (TSDR). DNA methylation analysis of the TSDR region of the gene FOXP3 was evaluated by quantitative PCR after bisulfite treatment of genomic DNA as previously described by Christopher Fuhrman (Fuhrman et al, Divergent Phenotypes of Human Regulatory T Cells Expressing the Receptors TIGIT and CD226, 2015, Journal of immunology). Briefly Nucleotides were isolated with AllPrep DNA/RNA Mini Kit (Qiagen) or DNeasy tissue kit (Qiagen), as appropriate. Bisulfite treatment of genomic DNA was performed on 500 ng DNA with the EZ DNA Methylation Kit (Zymo Research). DNA standards originated from unmethylated bisulfite-converted human EpiTect control DNA (Qiagen) or universally methylated bisulfite-converted human control DNA (Zymo Research). To obtain a large quantity of standard, the TSDR was PCR-amplified using the following reaction: 50 μl reaction volume containing 25 μl of ZymoTaq PreMix buffer (Zymo Research) and 0.5 μM each of the primers FOXP3_TSDRfwd (5'-ATATTTTAGATAGGGA-TATGGAGATGATTTGTTTGG-3' SEQ ID NO: 1) and FOXP3_TSDRrev (5'-AATAAACATCACCTACCACATC-CACCAACAC-3'-SEQ ID NO: 2). After incubation at 95° C. for 10 min, amplification was performed as follows: 50 cycles at 95° C. for 30 s, 55° C. for 30 s, and 72° C. for 1 min. Amplified PCR products were purified with the QIAquick Gel Extraction Kit (Qiagen). The concentration of purified control TSDR DNA was determined with a GE NanoVue spectrophotometer (GE Healthcare Life Sciences). TSDR real-time PCR was performed with probes that targeted methylated or demethylated target sequences. The reaction was performed in 96-well white trays with a Roche LightCycler 480 system (Roche Diagnostics). Each reaction contained 10 μl LightCycler 480 Probes Master Mix (Roche), 10 ng of bisulfite converted DNA sample or standards, 1 μM of each primer, and 150 nM of each probe with a final reaction value of 20 μl. The probes used for amplification were TSDR-Forward 5'-GGTTTGTAT-TTGGGTTTTGTTGTTATAGT-3' (SEQ ID NO: 3) and TSDR-Reverse 5'-CTATAAAATAAAATATC-TACCCTCTTCTCTTCCT-3' (SEQ ID NO: 4). The probes for target sequence detection were FAM-labeled methylated probe, FAM-CGGTCGGATGCGTC-MGB-NFQ (SEQ ID NO: 5), or VIC-labeled unmethylated probe, VIC-TGGTGGTTGGATGTGTTG-MGB-NFQ (SEQ ID NO: 6). All samples were tested in triplicate. The protocol for real-time amplification is as follows: after initial denaturation at 95° C. for 10 min, the samples were subjected to 50 cycles at 95° C. for 15 s and at 61° C. for 1 min. Fourteen different ratios of fully methylated and demethylated template were used as real-time standards. A six-order polynomial equation was used to extrapolate the percentage of cells demethylated at the TSDR for each sample.

Measurement of histone acetylation: Histone acetylation analysis of the four different sites of FOXP3 gene was evaluated by ChIP assay, as previously described by Ling Lu (Ling Lu et al, PNAS 2014). Briefly, 50,000 cells of each treated nTreg cell sample were harvested and cross-linked with 1% formaldehyde, and then lysed with 120 μL of lysis buffer [50 mM Tris.HCl, pH 8.0, 10 mM EDTA, 1% (wt/vol) SDS, protease inhibitor mix (1:100 dilution; Sigma), 1 mM PMSF, 20 mM Na-butyrate]. The chromatin in the lysate was sonicated to 500-800-bp fragments and then diluted with 800 μL of RIPA ChIP buffer [10 mM Tris.HCl, pH 7.5, 140 mM NaCl, 1 mM EDTA, 0.5 mM EGTA, 1% (vol/vol) Triton X-100, 0.1% (wt/vol) SDS, 0.1% (wt/vol) Na-deoxycholate, protease inhibitor mix (1:100 dilution; Sigma), 1 mM PMSF, and 20 mM Na-butyrate]. Dynabeads protein G (10 μL; Invitrogen) was incubated with 1 μg of H3K4me3 (Abcam) or H3K9ac (Cell Signaling) or normal rabbit IgG negative control ChIP-grade antibodies for 2 h separately. Then, 100 μL of the sheared chromatin was immunoprecipitated with pretreated antibody-bead complexes and another 100 μL of the sheared chromatin for total input DNA extraction separately. Immunoprecipitated DNA was quantified by real-time PCR with following primers: promoter, 5'-ACC GTA CAG CGT GGT TTT TC-3' (SEQ ID NO: 7) and 5'-CTA CCT CCC TGC CAT CTC CT-3' (SEQ ID NO: 8); CNS1,5'-CCC AAG CCC TAT GTG TGATT-3' (SEQ ID NO: 9) and 5'-GTG TGT CAG GCC TTG TGC TA-3' (SEQ ID NO: 10); CNS2,5'-GTC CTC TCC ACAACC CAA GA-3' (SEQ ID NO: 11) and 5'-GAC ACC ACG GAG GAA GAG AA-3' (SEQ ID NO: 12); and CNS3,5'-AGG TGC CGA CCT TTA CTG TG-3' (SEQ ID NO: 13) and 5'-ACA ATA CGG CCT CCT CCT CT-3' (SEQ ID NO: 14).

Results a) Induction of Foxp3$^+$ Expression in Ex Vivo Human Induced Tumor-Antigen Specific CD4$^+$ TCRγδ Unrestricted T Cells.

Figure 2:
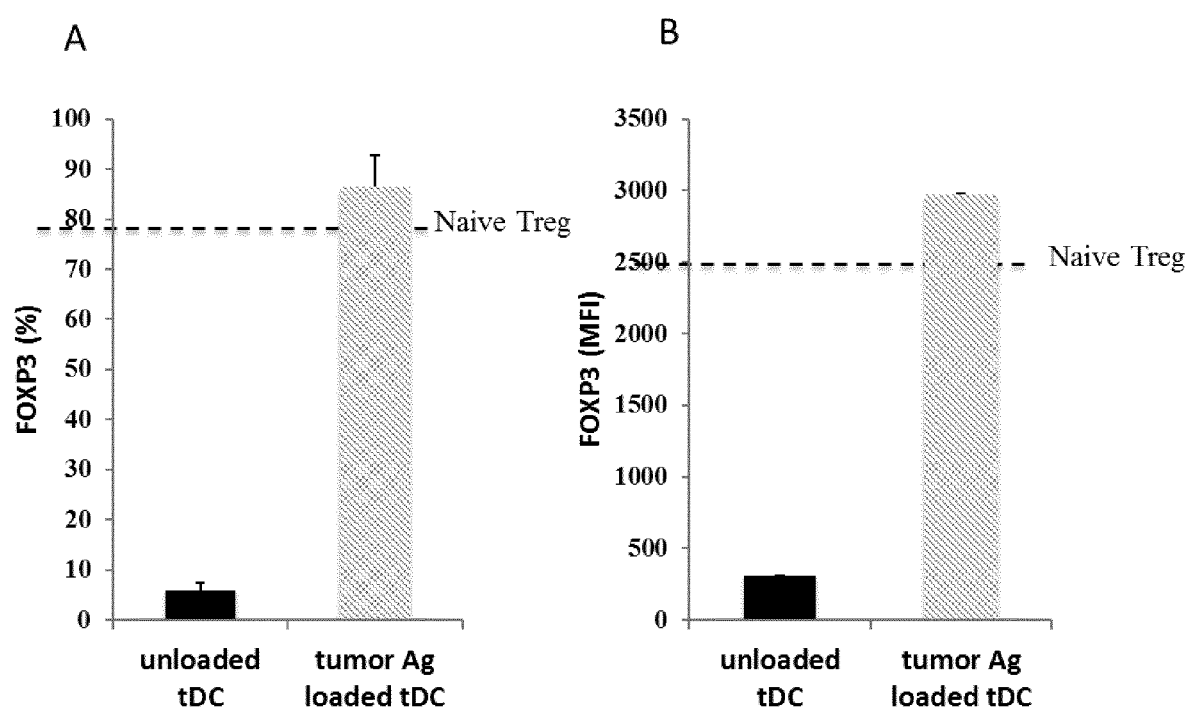
FIG. 2: Analysis of Foxp3+ expression in ex vivo human induced tumor-antigen specific FOXP3 expressing CD4+ TCRγδ+ unrestricted T cells. Apoptotic tumor antigen (Ag)-pulsed tolerogenic DCs (tDCs) were used to generate and expand specific pTreg from naive CD4+ T cells in the presence of IL-2 (100 IU/ml) and the nTreg polarizing medium composed of TGFβ (5 ng/ml), PGE2 (1 μM) and Rapa (10 nM). Unloaded tDC were used as control. (A)

Optimal conditions are set up for inducing tumor-antigen specific FOXP3$^+$ expressing CD4$^+$ TCRγδ unrestricted T cells, as described before. FIG. 2 shows that apoptotic tumor antigen-pulsed tolerogenic DCs ("tumor Ag loaded tDC"), in presence of IL-2 and the nTreg polarizing medium composed of TGFβ, PGE2 and rapamycin are able to induce high levels of Foxp3$^+$ expression (in frequency in FIG. 2A and in MFI in FIG. 2B) in antigen specific stimulated naive conventional CD4$^+$ T cells ("Naïve Treg"), while non-pulsed tDCs ("unloaded tDC"), in presence of the same polarizing medium, are unable to induce Foxp3+ expression in naive conventional CD4$^+$ T cells.

b) Specific Recruitment of Pathogenic CD4$^+$ γδ T Cells Expressing Foxp3 in Human Breast Cancer.

A novel γδ T cells' subset exhibiting CD4 and Foxp3 expression has been identified in the TIL isolated from breast cancer (BC) biopsies. Indeed, while γδ T cells expression Foxp3 are rare in PBMCs from normal individuals (<1%), they are strongly enriched in the TIL purified from BC biopsies (around 10-fold) as shown in FIG. 3.

As generally human γδT cells are divided into two major structural subsets according to their TCR δ chain usage: Vδ1 and Vδ2 T cells, Vδ1 being the predominant tissue resident cells whereas Vδ2 the major subset in peripheral blood, we have investigated the TCR Vδ chain in this new CD4$^+$ Foxp3+ γδT subset by flow cytometry. FIG. 4 shows that most of the pathogenic CD4+ γδ T cells expressing Foxp3 (>85%) are Vδ1negVδ2neg.

We have next evaluated the functional suppressive capacity of the Foxp3 expressing CD3+ CD4+ γδ T cells unrestricted T cells isolated from BC biopsies. FIG. 5 shows that, similar to fresh Treg, these CD4+ γδ T cells expressing FOXP3+ display suppressive activity when using the standard polyclonal cell-cell contact Treg suppression assay.

c) Induction of Autologous CD8-Mediated T-Cell Responses Against Tumor-Antigen Specific FOXP3 Expressing CD4+ TCRγδ Unrestricted T Cells.

A culture system is established in which inflammatory DC (inf DC) loaded with apoptotic pathogenic CD4+ T cells cocultured with autologous CD3+ naïve T cells are able to induce the generation of CD8+ T-cell lines against pathogenic CD4+ T cells used to load the dendritic cells. FIG. 6 shows that the two CD8+ clones induced with apoptotic pathogenic CD4+ T cells loaded—inf DC ("mDC") or—TAP-inhibited DC respectively are able to lyse their specific targets, their inducing pathogenic CD4+ T cell clone. However, when both CD8+ clones are tested against an autologous EBV cell line, they are unable to lyse this target (FIG. 6).

d) Presence of FOXP3+ Expressing T Cells in Tumor Infiltrating Lymphocytes (TILs) Isolated from Luminal B Breast Cancer.

Luminal A and B subtypes are both estrogen-receptor-positive (ER+) and low-grade, with luminal A tumors growing very slowly and luminal B tumors growing more quickly. Luminal A tumors have the best prognosis. Luminal B tumors are associated with a poor clinical outcome. We examined by flow cytometry the phenotype of lymphocytes in the TIL isolated from both luminal subtypes breast cancer and found the presence of Foxp3 expression in CD3+ CD4+ TCRαβ+ MHCII restricted and CD3+ CD4+ TCRγδ+ unrestricted T cells. No Foxp3 was detected in TILs extracted from luminal A breast tumor (FIG. 7). Moreover, a positive correlation is observed between a high percentage of Foxp3 expression in CD3+ CD4+ TCRγδ+ unrestricted T cells and a poor clinical outcome in breast cancer (FIG. 8).

Foxp3 expressing CD3+ CD4+ TCRαβ+ MHCII restricted T cells and Foxp3 expressing CD3+ TCRαβ+ unrestricted T cells represent approximately 20% of the CD3+ TCRαβ T cells and 23% of the CD3+ TCRγδ+ respectively in the studied sample. Foxp3 expressing CD3+ TCRγδ+ T cells present a same phenotypic profile as Foxp3+ CD3+ TCRαβ+ T cells. These Foxp3+ TCRγδ+ T cell population express levels of Foxp3, CD25 and CTLA4 similar to those of Foxp3+ CD3+ TCRαβ+ T cells (FIG. 9).

d) Ex Vivo Generation and Expansion of Specific CD3+ TCRγδ+ Expressing Foxp3 Committed to Exclusively Exert Regulatory Activity.

As studies suggested that the suppressive potential of antigen-specific Treg was much greater than that of polyclonal Treg, we set up a method to ex vivo generated and expanded antigen specific Foxp3 expressing CD3+ TCRγδ+ unrestricted T cells, committed to exclusively exert regulatory activity, whichever culture condition of stimulation is.

FIG. 10 shows that naive CD3+ TCRγδ+ T cells (CD3+ CD45RA+ CD27+ TCRγδ+ T cells) stimulated with zoledronic acid-treated-autologous tDCs, in presence of the nTreg polarizing medium comprising the combination of IL-15, IL-2, TGFβ, PGE2 and rapamycin, express Foxp3 after 21 days expansion and exhibit significant functional suppressive activity, as assessed by the standard polyclonal cell-cell contact Treg suppression assay. Interestingly the 21-day-expanded FOXP3 expressing CD3+ TCR γδ+ T cells maintain their Foxp3 level and their suppressive activity, after a further 21-day-culture in nTreg polarizing medium.

The invention claimed is:

1. A method for generating ex vivo γδ Foxp3+ regulatory T cells having the following phenotype: CD3+ TCRγδ+ Foxp3+, comprising culturing CD3+ TCRγδ+ T cells in the presence of a γδ T cell activator and the following agents: i) an cAMP (Cyclic adenosine monophosphate) activator, wherein the cAMP activator is selected from the group consisting of prostaglandin E2 (PGE2), an EP2 or EP4 agonist, a membrane adenine cyclase activator and a metabotropic glutamate receptors agonist, ii) a TGFβ (Transforming growth factor beta) pathway activator, wherein the TGFβ pathway activator is selected from the group consisting of TGFβ, bone morphogenetic proteins (BMPs), growth and differentiation factors (GDFs), anti-müllerian hormone (AMH), activin and nodal, and iii) a mTOR inhibitor, wherein the mTOR inhibitor is selected from the group consisting of rapamycin, rapamycin analogs, wortmannin; theophylline; caffeine; epigallocatechin gallate (EGCG), curcumin, resveratrol; genistein, 3,3-diindolylmethane (DIM), LY294002 (2-(4-morpholinyl)-8-phenyl-4H-1-benzopyran-4-one), PP242, PP30, Torin1, Ku-0063794, WAY-600, WYE-687, WYE-354, GNE477, NVP-BEZ235, PI-103, XL765 and WJD008, and optionally iv) at least one cytokine selected from the group consisting of IL-2, IL-7, IL-15 and TSLP, and/or v) at least one TET enzyme activator selected from the group consisting of vitamin C and a NaHS hydrogen sulfide releasing agent and/or vi) at least one DNMT inhibitor selected from the group consisting of 2-(1,3-dioxo-1,2-dihydro-2H-isoindol- 2-yl)-3-(1H-indol-3-yl) propanoic acid (RG108), 5-aza-22-deoxycytidine (DAC) and 5-azacytidine (SAC), for at least 5 days, wherein the γδ T cell activator is an antigen-specific γδ T cell activator comprising tolerogenic dendritic cells (DCs) pulsed with at least one bisphosphonate and wherein the tolerogenic DCs are pulsed with the at least one bisphosphonate prior to being added to the $CD3^+$ $TCR\gamma\delta^+$ T cells.

2. The method according to claim 1, further comprising an expansion step, wherein the γδ $Foxp3^+$ regulatory T cells are cultured in the presence of a γδ T cell activator and the following agents: i) an cAMP (Cyclic adenosine monophosphate) activator, ii) a TGFβ (Transforming growth factor beta) pathway activator, iii) a mTOR inhibitor, and optionally iv) at least one cytokine selected from the group consisting of IL-2, IL-7, IL-15 and TSLP, and optionally v) at least one TET enzymes activator and/or at least one DNMT inhibitor, for at least 5 days, wherein the γδ T cell activator, the cAMP activator, the TGFβ pathway activator, the mTOR inhibitor, the TET enzymes activator, and the DNMT inhibitor are as defined in claim 1.

3. The method of claim 1, wherein the at least one bisphosphonate comprises at least one aminobisphosphonate.

4. The method of claim 1, wherein the tolerogenic DCs are derived from monocytes.

* * * * *

SEQUENCE LISTING

<160> NUMBER OF SEQ ID NOS: 14

<210> SEQ ID NO 1
<211> LENGTH: 37
<212> TYPE: DNA
<213> ORGANISM: Artificial Sequence
<220> FEATURE:
<223> OTHER INFORMATION: Synthetic primers FOXP3_TSDR fwd

<400> SEQUENCE: 1 atattttag atagggatat ggagatgatt tgtttgg        37

<210> SEQ ID NO 2
<211> LENGTH: 31
<212> TYPE: DNA
<213> ORGANISM: Artificial Sequence
<220> FEATURE:
<223> OTHER INFORMATION: Synthetic FOXP3_TSDR rev

<400> SEQUENCE: 2
aataaacatc acctaccaca tccaccaaca c            31

<210> SEQ ID NO 3
<211> LENGTH: 29
<212> TYPE: DNA
<213> ORGANISM: Artificial Sequence
<220> FEATURE:
<223> OTHER INFORMATION: Synthetic TSDR-Forward

```
<400> SEQUENCE: 3
ggtttgtatt tgggttttgt tgttatagt                                      29

<210> SEQ ID NO 4
<211> LENGTH: 34
<212> TYPE: DNA
<213> ORGANISM: Artificial Sequence
<220> FEATURE:
<223> OTHER INFORMATION: Synthetic TSDR-Reverse

<400> SEQUENCE: 4
ctataaaata aaatatctac cctcttctct tcct                                34

<210> SEQ ID NO 5
<211> LENGTH: 14
<212> TYPE: DNA
<213> ORGANISM: Artificial Sequence
<220> FEATURE:
<223> OTHER INFORMATION: Synthetic FAM-labeled methylated probe

<400> SEQUENCE: 5
cggtcggatg cgtc                                                      14

<210> SEQ ID NO 6
<211> LENGTH: 18
<212> TYPE: DNA
<213> ORGANISM: Artificial Sequence
<220> FEATURE:
<223> OTHER INFORMATION: Synthetic VIC-labeled unmethylated probe

<400> SEQUENCE: 6
tggtggttgg atgtgttg                                                  18

<210> SEQ ID NO 7
<211> LENGTH: 20
<212> TYPE: DNA
<213> ORGANISM: Artificial Sequence
<220> FEATURE:
<223> OTHER INFORMATION: Synthetic primer promoter

<400> SEQUENCE: 7
accgtacagc gtggttttc                                                 20

<210> SEQ ID NO 8
<211> LENGTH: 20
<212> TYPE: DNA
<213> ORGANISM: Artificial Sequence
<220> FEATURE:
<223> OTHER INFORMATION: Synthetic primer promoter

<400> SEQUENCE: 8
ctacctccct gccatctcct                                                20

<210> SEQ ID NO 9
<211> LENGTH: 20
<212> TYPE: DNA
<213> ORGANISM: Artificial Sequence
<220> FEATURE:
<223> OTHER INFORMATION: Synthetic primer CNS1

<400> SEQUENCE: 9
cccaagccct atgtgtgatt                                                20

<210> SEQ ID NO 10
<211> LENGTH: 20
```

```
<212> TYPE: DNA
<213> ORGANISM: Artificial Sequence
<220> FEATURE:
<223> OTHER INFORMATION: Synthetic primer CNS1

<400> SEQUENCE: 10
gtgtgtcagg ccttgtgcta                                              20

<210> SEQ ID NO 11
<211> LENGTH: 20
<212> TYPE: DNA
<213> ORGANISM: Artificial Sequence
<220> FEATURE:
<223> OTHER INFORMATION: Synthetic primer CNS2

<400> SEQUENCE: 11
gtcctctcca caacccaaga                                              20

<210> SEQ ID NO 12
<211> LENGTH: 20
<212> TYPE: DNA
<213> ORGANISM: Artificial Sequence
<220> FEATURE:
<223> OTHER INFORMATION: Synthetic primer CNS2

<400> SEQUENCE: 12
gacaccacgg aggaagagaa                                              20

<210> SEQ ID NO 13
<211> LENGTH: 20
<212> TYPE: DNA
<213> ORGANISM: Artificial Sequence
<220> FEATURE:
<223> OTHER INFORMATION: Synthetic primer CNS3

<400> SEQUENCE: 13
aggtgccgac ctttactgtg                                              20

<210> SEQ ID NO 14
<211> LENGTH: 20
<212> TYPE: DNA
<213> ORGANISM: Artificial Sequence
<220> FEATURE:
<223> OTHER INFORMATION: Synthetic primer CNS3

<400> SEQUENCE: 14
acaatacggc ctcctcctct                                              20
```